(12) United States Patent
Chuang et al.

(10) Patent No.: US 10,313,622 B2
(45) Date of Patent: Jun. 4, 2019

(54) DUAL-COLUMN-PARALLEL CCD SENSOR AND INSPECTION SYSTEMS USING A SENSOR

(71) Applicant: KLA-Tencor Corporation, Milpitas, CA (US)

(72) Inventors: Yung-Ho Alex Chuang, Cupertino, CA (US); Jingjing Zhang, San Jose, CA (US); Sharon Zamek, Sunnyvale, CA (US); John Fielden, Los Altos, CA (US); Devis Contarato, San Carlos, CA (US); David L. Brown, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 96 days.

(21) Appl. No.: 15/337,604

(22) Filed: Oct. 28, 2016

(65) Prior Publication Data

US 2017/0295334 A1 Oct. 12, 2017

Related U.S. Application Data

(60) Provisional application No. 62/319,130, filed on Apr. 6, 2016.

(51) Int. Cl.
*H04N 5/378* (2011.01)
*G01N 21/95* (2006.01)
(Continued)

(52) U.S. Cl.
CPC ......... *H04N 5/378* (2013.01); *G01N 21/9501* (2013.01); *G06T 7/0008* (2013.01);
(Continued)

(58) Field of Classification Search
CPC .......... H04N 5/378; G01N 21/00; G03F 7/00; H01L 21/00; G01B 11/00
See application file for complete search history.

(56) References Cited

U.S. PATENT DOCUMENTS 3,699,646 A 10/1972 Vadasz et al.
3,870,917 A 3/1975 Cuny
(Continued)

FOREIGN PATENT DOCUMENTS

EP 0543629 A1 5/1993
EP 0602983 A1 6/1994
(Continued)

OTHER PUBLICATIONS

U.S. Appl. No. 61/720,700—Certified Copy corres to PCT/EP2013/071080, pp. 1-44.
(Continued)

*Primary Examiner* — Clifford Hilaire
(74) *Attorney, Agent, or Firm* — Bever, Hoffman & Harms, LLP

(57) ABSTRACT

A dual-column-parallel image CCD sensor utilizes a dual-column-parallel readout circuit including two pairs of cross-connected transfer gates to alternately transfer pixel data (charges) from a pair of adjacent pixel columns to a shared output circuit at high speed with low noise. Charges transferred along the two adjacent pixel columns at a line clock rate are alternately passed by the transfer gates to a summing gate that is operated at twice the line clock rate to pass the image charges to the shared output circuit. A symmetrical Y-shaped diffusion is utilized in one embodiment to merge the image charges from the two pixel columns. A method of driving the dual-column-parallel CCD sensor with line clock
(Continued)

synchronization is also described. A method of inspecting a sample using the dual-column-parallel CCD sensor is also described.

12 Claims, 19 Drawing Sheets

(51) Int. Cl.
*G06T 7/00* (2017.01)
*H01L 27/148* (2006.01)
*H04N 5/372* (2011.01)
*H04N 5/361* (2011.01)

(52) U.S. Cl.
CPC .. *H01L 27/14812* (2013.01); *H01L 27/14825* (2013.01); *H04N 5/361* (2013.01); *H04N 5/372* (2013.01); *G06T 2207/30148* (2013.01)

(56) References Cited

U.S. PATENT DOCUMENTS

| | | | |
|---|---|---|---|
| 3,914,748 A * | 10/1975 | Barton | G11C 19/287 257/243 |
| 3,947,707 A | 3/1976 | Shannon et al. | |
| 4,099,198 A | 7/1978 | Howorth et al. | |
| 4,106,046 A | 8/1978 | Nathanson et al. | |
| 4,210,922 A | 7/1980 | Shannon | |
| 4,275,326 A | 6/1981 | Houtkamp | |
| 4,280,141 A | 7/1981 | McCann et al. | |
| 4,348,690 A | 9/1982 | Jastrzebski et al. | |
| 4,382,267 A | 5/1983 | Angle | |
| 4,467,189 A | 8/1984 | Tsuchiya | |
| 4,555,731 A | 11/1985 | Zinchuk | |
| 4,580,155 A | 4/1986 | Tsoi et al. | |
| 4,644,221 A | 2/1987 | Gutierrez et al. | |
| 4,760,031 A | 7/1988 | Janesick | |
| 4,853,595 A | 8/1989 | Alfano et al. | |
| 4,999,014 A | 3/1991 | Gold et al. | |
| 5,054,683 A | 10/1991 | Haisma et al. | |
| 5,120,949 A | 6/1992 | Tomasetti | |
| 5,144,630 A | 9/1992 | Lin | |
| 5,181,080 A | 1/1993 | Fanton et al. | |
| 5,227,313 A | 7/1993 | Gluck et al. | |
| 5,315,126 A | 5/1994 | Field | |
| 5,376,810 A | 12/1994 | Hoenk et al. | |
| 5,428,392 A | 6/1995 | Castro et al. | |
| 5,440,648 A | 8/1995 | Roberts et al. | |
| 5,483,378 A | 1/1996 | Rahn | |
| 5,563,702 A | 10/1996 | Emery et al. | |
| 5,608,526 A | 3/1997 | Piwonka-Corle et al. | |
| 5,684,583 A | 11/1997 | Abe et al. | |
| 5,717,518 A | 2/1998 | Shafer et al. | |
| 5,719,069 A | 2/1998 | Sparks | |
| 5,731,584 A | 3/1998 | Beyne et al. | |
| 5,742,626 A | 4/1998 | Mead et al. | |
| 5,760,809 A | 6/1998 | Malhotra et al. | |
| 5,760,899 A | 6/1998 | Eismann | |
| 5,812,190 A | 9/1998 | Audier et al. | |
| 5,852,322 A | 12/1998 | Speckbacher | |
| 5,877,859 A | 3/1999 | Aspnes et al. | |
| 5,940,685 A | 8/1999 | Loomis et al. | |
| 5,965,910 A | 10/1999 | Wood | |
| 5,999,310 A | 12/1999 | Shafer et al. | |
| 6,013,399 A | 1/2000 | Nguyen | |
| 6,030,852 A | 2/2000 | Sano et al. | |
| 6,064,759 A | 5/2000 | Buckley et al. | |
| 6,162,707 A | 12/2000 | Dinh et al. | |
| 6,201,601 B1 | 3/2001 | Vaez-Iravani et al. | |
| 6,271,916 B1 | 8/2001 | Marxer et al. | |
| 6,278,119 B1 | 8/2001 | Nikzad et al. | |
| 6,285,018 B1 | 9/2001 | Aebi et al. | |
| 6,297,879 B1 | 10/2001 | Yang et al. | |
| 6,297,880 B1 | 10/2001 | Rosencwaig et al. | |
| 6,307,586 B1 | 10/2001 | Costello | |
| 6,346,700 B1 | 2/2002 | Cunningham et al. | |
| 6,362,484 B1 | 3/2002 | Beyne et al. | |
| 6,373,869 B1 | 4/2002 | Jacob | |
| 6,403,963 B1 | 6/2002 | Nikzad et al. | |
| 6,429,943 B1 | 8/2002 | Opsal et al. | |
| 6,456,318 B1 | 9/2002 | Noguchi | |
| 6,535,531 B1 | 3/2003 | Smith et al. | |
| 6,545,281 B1 | 4/2003 | McGregor et al. | |
| 6,608,676 B1 | 8/2003 | Zhao et al. | |
| 6,711,283 B1 | 3/2004 | Soenksen | |
| 6,837,766 B2 | 1/2005 | Costello | |
| 7,005,637 B2 | 2/2006 | Costello et al. | |
| 7,039,157 B2 | 5/2006 | Fujii et al. | |
| 7,046,283 B1 | 5/2006 | Kamasz et al. | |
| 7,126,699 B1 | 10/2006 | Wihl et al. | |
| 7,130,039 B2 | 10/2006 | Vaez-Iravani et al. | |
| 7,136,159 B2 | 11/2006 | Tsai et al. | |
| 7,141,791 B2 | 11/2006 | Masnaghetti et al. | |
| 7,227,984 B2 | 6/2007 | Cavan | |
| 7,233,350 B2 | 6/2007 | Tay | |
| 7,283,166 B1 | 10/2007 | Billman | |
| 7,313,155 B1 | 12/2007 | Mu et al. | |
| 7,321,468 B2 | 1/2008 | Herkommer et al. | |
| 7,345,825 B2 | 3/2008 | Chuang et al. | |
| 7,352,457 B2 | 4/2008 | Kvamme et al. | |
| 7,432,517 B2 | 10/2008 | Botma et al. | |
| 7,446,474 B2 | 11/2008 | Maldonado et al. | |
| 7,465,935 B2 | 12/2008 | Urano et al. | |
| 7,471,315 B2 | 12/2008 | Silsby et al. | |
| 7,525,649 B1 | 4/2009 | Leong et al. | |
| 7,528,943 B2 | 5/2009 | Brown et al. | |
| 7,586,108 B2 | 9/2009 | Nihtianov et al. | |
| 7,609,303 B1 | 10/2009 | Lee et al. | |
| 7,609,309 B2 * | 10/2009 | Brown | H04N 5/372 348/295 |
| 7,714,287 B1 | 5/2010 | James et al. | |
| 7,741,666 B2 | 6/2010 | Nozaki et al. | |
| 7,750,280 B2 | 7/2010 | Hwang et al. | |
| 7,791,170 B2 | 9/2010 | Chiang et al. | |
| 7,800,040 B2 | 9/2010 | Blacksberg et al. | |
| 7,813,406 B1 | 10/2010 | Nguyen et al. | |
| 7,838,833 B1 | 11/2010 | Lent et al. | |
| 7,875,948 B2 | 1/2011 | Hynecek et al. | |
| 7,928,382 B2 | 4/2011 | Hatakeyama et al. | |
| 7,952,633 B2 | 5/2011 | Brown et al. | |
| 7,957,066 B2 | 6/2011 | Armstrong et al. | |
| 7,985,658 B2 | 7/2011 | Lei et al. | |
| 7,999,342 B2 | 8/2011 | Hsu et al. | |
| 8,017,427 B2 | 9/2011 | Manabe | |
| 8,138,485 B2 | 3/2012 | Nihtianov et al. | |
| 8,309,443 B2 | 11/2012 | Tanaka et al. | |
| 8,323,406 B2 | 12/2012 | Bondokov et al. | |
| 8,450,820 B2 | 5/2013 | Nanver et al. | |
| 8,455,971 B2 | 6/2013 | Chen et al. | |
| 8,513,587 B2 | 8/2013 | Wang et al. | |
| 8,514,587 B2 | 8/2013 | Zhang et al. | |
| 8,629,384 B1 | 1/2014 | Biellak et al. | |
| 8,686,331 B2 | 4/2014 | Armstrong | |
| 8,754,972 B2 | 6/2014 | Brown et al. | |
| 8,755,417 B1 | 6/2014 | Dribinski | |
| 8,873,596 B2 | 10/2014 | Dribinski et al. | |
| 8,929,406 B2 | 1/2015 | Chuang et al. | |
| 9,055,246 B2 | 6/2015 | Tay | |
| 9,077,862 B2 | 7/2015 | Brown et al. | |
| 9,131,175 B2 | 9/2015 | Kondou et al. | |
| 9,279,774 B2 | 3/2016 | Romanovsky et al. | |
| 9,282,271 B2 | 3/2016 | Hashimoto et al. | |
| 9,426,400 B2 | 8/2016 | Brown et al. | |
| 9,478,402 B2 | 10/2016 | Chuang et al. | |
| 9,496,425 B2 | 11/2016 | Chern et al. | |
| 9,529,182 B2 | 12/2016 | Chuang et al. | |
| 9,891,177 B2 | 2/2018 | Vazhaeparambil et al. | |
| 2001/0012069 A1 | 8/2001 | Derndinger et al. | |
| 2001/0017344 A1 | 8/2001 | Aebi | |
| 2001/0024684 A1 | 9/2001 | Steiner et al. | |
| 2001/0055424 A1 | 12/2001 | Publicover | |
| 2002/0191834 A1 | 12/2002 | Fishbaine | |
| 2003/0111707 A1 | 6/2003 | Takaura et al. | |

(56) References Cited

U.S. PATENT DOCUMENTS

| | | | |
|---|---|---|---|
| 2003/0210392 A1* | 11/2003 | Vaez-Iravani | G01N 21/8806 356/237.2 |
| 2003/0222579 A1 | 12/2003 | Habib et al. | |
| 2004/0012684 A1 | 1/2004 | Tinnerino | |
| 2004/0021061 A1 | 2/2004 | Bijkerk | |
| 2004/0032628 A1 | 2/2004 | Sato et al. | |
| 2004/0056279 A1 | 3/2004 | Niigaki et al. | |
| 2004/0074261 A1 | 4/2004 | Caron et al. | |
| 2004/0212708 A1 | 10/2004 | Spartiotis et al. | |
| 2004/0227070 A1 | 11/2004 | Bateman et al. | |
| 2005/0122021 A1 | 6/2005 | Smith et al. | |
| 2005/0167575 A1 | 8/2005 | Benz et al. | |
| 2005/0168602 A1 | 8/2005 | Sumi et al. | |
| 2005/0196059 A1 | 9/2005 | Inoue et al. | |
| 2005/0224842 A1* | 10/2005 | Toyama | H01L 27/14831 257/225 |
| 2005/0255625 A1 | 11/2005 | Janesick et al. | |
| 2005/0264148 A1 | 12/2005 | Maldonado et al. | |
| 2005/0287479 A1 | 12/2005 | Moon et al. | |
| 2006/0054778 A1 | 3/2006 | Suhling | |
| 2006/0069460 A1 | 3/2006 | Smith et al. | |
| 2006/0087649 A1 | 4/2006 | Ogawa et al. | |
| 2006/0170324 A1 | 8/2006 | Machuca et al. | |
| 2006/0188869 A1 | 8/2006 | Zeskind et al. | |
| 2007/0007429 A1 | 1/2007 | Fairley et al. | |
| 2007/0023770 A1 | 2/2007 | Miyajima et al. | |
| 2007/0034987 A1 | 2/2007 | Costello et al. | |
| 2007/0072326 A1 | 3/2007 | Zheng et al. | |
| 2007/0096648 A1 | 5/2007 | Nakajima et al. | |
| 2007/0103769 A1 | 5/2007 | Kuwabara | |
| 2007/0138378 A1 | 6/2007 | Chang et al. | |
| 2007/0171298 A1 | 7/2007 | Kurane | |
| 2007/0177289 A1 | 8/2007 | Shim et al. | |
| 2007/0188744 A1 | 8/2007 | Leslie et al. | |
| 2007/0210395 A1 | 9/2007 | Maruyama et al. | |
| 2007/0229677 A1 | 10/2007 | Mochizuki et al. | |
| 2007/0291810 A1 | 12/2007 | Luo et al. | |
| 2008/0002037 A1 | 1/2008 | Ueda | |
| 2008/0044932 A1 | 2/2008 | Samoilov et al. | |
| 2008/0068593 A1 | 3/2008 | Nakano et al. | |
| 2008/0074513 A1 | 3/2008 | Noguchi | |
| 2008/0079830 A1 | 4/2008 | Lepage | |
| 2008/0173903 A1 | 7/2008 | Imai et al. | |
| 2008/0232674 A1 | 9/2008 | Sakai et al. | |
| 2008/0267241 A1 | 10/2008 | Brown et al. | |
| 2008/0278775 A1 | 11/2008 | Katzir et al. | |
| 2008/0315092 A1 | 12/2008 | Kley | |
| 2009/0009645 A1 | 1/2009 | Schrey et al. | |
| 2009/0079973 A1 | 3/2009 | Uto et al. | |
| 2009/0080759 A1 | 3/2009 | Bhaskar et al. | |
| 2009/0091752 A1 | 4/2009 | Terasawa et al. | |
| 2009/0108207 A1 | 4/2009 | Liu | |
| 2009/0125242 A1 | 5/2009 | Choi et al. | |
| 2009/0128912 A1 | 5/2009 | Okada et al. | |
| 2009/0168152 A1 | 7/2009 | Gelernt et al. | |
| 2009/0180176 A1 | 7/2009 | Armstrong et al. | |
| 2009/0322903 A1 | 12/2009 | Hashimoto et al. | |
| 2010/0026865 A1 | 2/2010 | Tivarus et al. | |
| 2010/0038540 A1 | 2/2010 | Hannebauer | |
| 2010/0102213 A1 | 4/2010 | Garris | |
| 2010/0103409 A1 | 4/2010 | Ohshima et al. | |
| 2010/0104173 A1 | 4/2010 | Yoshida et al. | |
| 2010/0140675 A1 | 6/2010 | Rhodes | |
| 2010/0148667 A1 | 6/2010 | Niigaki et al. | |
| 2010/0188655 A1 | 7/2010 | Brown et al. | |
| 2010/0194956 A1 | 8/2010 | Yuan et al. | |
| 2010/0208979 A1 | 8/2010 | Abbott et al. | |
| 2010/0301437 A1 | 12/2010 | Brown | |
| 2010/0309308 A1 | 12/2010 | Saphier et al. | |
| 2011/0019044 A1 | 1/2011 | Wang et al. | |
| 2011/0062499 A1 | 3/2011 | Burke | |
| 2011/0073982 A1 | 3/2011 | Armstrong et al. | |
| 2011/0101219 A1 | 5/2011 | Uchiyama et al. | |
| 2011/0116077 A1 | 5/2011 | Chuang et al. | |
| 2011/0168886 A1 | 7/2011 | Shadman et al. | |
| 2011/0234790 A1 | 9/2011 | True | |
| 2011/0256655 A1 | 10/2011 | Nikzad et al. | |
| 2011/0261354 A1 | 10/2011 | Sinfield et al. | |
| 2011/0279725 A1 | 11/2011 | Cazaux et al. | |
| 2011/0291109 A1 | 12/2011 | Wraback et al. | |
| 2012/0012811 A1 | 1/2012 | Deflumere et al. | |
| 2012/0012957 A1 | 1/2012 | Larsen et al. | |
| 2012/0038809 A1 | 2/2012 | Lee et al. | |
| 2012/0081684 A1 | 4/2012 | Den Oef et al. | |
| 2012/0132823 A1 | 5/2012 | Menge et al. | |
| 2012/0160993 A1 | 6/2012 | Nevet et al. | |
| 2012/0170021 A1 | 7/2012 | Walsh | |
| 2012/0228485 A1 | 9/2012 | Iwakiri et al. | |
| 2012/0268722 A1 | 10/2012 | Nihtianov et al. | |
| 2013/0009069 A1 | 1/2013 | Okada | |
| 2013/0015324 A1 | 1/2013 | Park et al. | |
| 2013/0016346 A1 | 1/2013 | Romanovsky et al. | |
| 2013/0017205 A1 | 1/2013 | Giaccia et al. | |
| 2013/0020491 A1 | 1/2013 | Mazzillo | |
| 2013/0056843 A1 | 3/2013 | Lee et al. | |
| 2013/0077086 A1 | 3/2013 | Chuang et al. | |
| 2013/0082241 A1 | 4/2013 | Kub et al. | |
| 2013/0088706 A1 | 4/2013 | Chuang et al. | |
| 2013/0114085 A1 | 5/2013 | Wang et al. | |
| 2013/0126705 A1 | 5/2013 | Maleev | |
| 2013/0148112 A1 | 6/2013 | Chuang et al. | |
| 2013/0149807 A1 | 6/2013 | Jangjian et al. | |
| 2013/0169957 A1 | 7/2013 | Wolf et al. | |
| 2013/0176552 A1 | 7/2013 | Brown et al. | |
| 2013/0270663 A1 | 10/2013 | Lin et al. | |
| 2013/0313440 A1 | 11/2013 | Chuang et al. | |
| 2013/0320211 A1 | 12/2013 | Park et al. | |
| 2013/0336574 A1 | 12/2013 | Nasser-Ghodsi et al. | |
| 2013/0341504 A1 | 12/2013 | Neill et al. | |
| 2014/0034816 A1 | 2/2014 | Chuang et al. | |
| 2014/0111799 A1 | 4/2014 | Lei et al. | |
| 2014/0151552 A1 | 6/2014 | Jiang et al. | |
| 2014/0158864 A1* | 6/2014 | Brown | H04N 5/3742 250/208.1 |
| 2014/0203386 A1 | 7/2014 | Bui et al. | |
| 2014/0204427 A1* | 7/2014 | Nakazawa | H04N 5/3692 358/445 |
| 2014/0246595 A1 | 9/2014 | Menge et al. | |
| 2014/0305367 A1 | 10/2014 | Chuang et al. | |
| 2014/0362203 A1 | 12/2014 | Delaney et al. | |
| 2015/0007765 A1 | 1/2015 | Dribinski | |
| 2015/0022699 A1 | 1/2015 | Shimada | |
| 2015/0136956 A1 | 5/2015 | Yin et al. | |
| 2015/0177159 A1 | 6/2015 | Brown et al. | |
| 2015/0200216 A1 | 7/2015 | Muramatsu et al. | |
| 2015/0237282 A1 | 8/2015 | Shimada | |
| 2015/0256778 A1 | 9/2015 | Kusaka | |
| 2015/0275393 A1 | 10/2015 | Bondokov et al. | |
| 2015/0294998 A1 | 10/2015 | Nihtianov et al. | |
| 2015/0304580 A1 | 10/2015 | Wang | |
| 2015/0358571 A1 | 12/2015 | Dominguez Castro et al. | |
| 2015/0365610 A1 | 12/2015 | Dominguez Castro et al. | |
| 2015/0369750 A1 | 12/2015 | Wang et al. | |
| 2016/0037110 A1 | 2/2016 | Choi et al. | |
| 2016/0050383 A1 | 2/2016 | Grauer et al. | |
| 2016/0056606 A1 | 2/2016 | Chuang et al. | |
| 2016/0142653 A1 | 5/2016 | Cho et al. | |
| 2016/0269657 A1 | 9/2016 | Nishihara | |
| 2017/0195596 A1 | 7/2017 | Vogelsang et al. | |
| 2017/0201698 A1* | 7/2017 | Parks | H04N 5/347 |

FOREIGN PATENT DOCUMENTS

| | | |
|---|---|---|
| EP | 0746871 A1 | 12/1996 |
| EP | 1538827 A1 | 6/2005 |
| EP | 1939917 A2 | 7/2008 |
| EP | 2088763 A2 | 8/2009 |
| EP | 2346094 A1 | 7/2011 |
| JP | H08241977 A | 9/1996 |
| JP | H10171965 A | 6/1998 |
| JP | H11153516 A | 6/1999 |
| JP | 2002033473 | 1/2002 |
| JP | 2004031452 A | 1/2004 |
| JP | 2007086108 A | 4/2007 |

(56) References Cited

FOREIGN PATENT DOCUMENTS

| | | | |
|---|---|---|---|
| JP | 2008096430 A | 4/2008 |
| JP | 2008224303 A | 9/2008 |
| JP | 2009117454 A | 5/2009 |
| JP | 5304674 B2 | 10/2013 |
| KR | 20020084541 A | 11/2002 |
| KR | 100688497 B1 | 3/2007 |
| KR | 100826407 B1 | 5/2008 |
| RU | 2297070 C2 | 4/2007 |
| WO | 9532518 A1 | 11/1995 |
| WO | 9600381 A1 | 1/1996 |
| WO | 9617372 A1 | 6/1996 |
| WO | 2007035858 A2 | 3/2007 |
| WO | 2008121232 A1 | 10/2008 |
| WO | 2011091159 A1 | 7/2011 |
| WO | 2014067754 A2 | 5/2014 |

OTHER PUBLICATIONS

Allen et al., Work Function, Photoelectric Threshold, and Surface . . . ; Physical Review, vol. 127, No. 1, Jul. 1, 1962, pp. 150-158.

Dulinski et al., Tests of a backside illuminated monolithic CMOS pixel . . . , Nuclear Instruments and Methods in Physics Research A 546 (2005) 274-280, 7 pgs.

Fanton et al, Multiparameter Measurements of Thin Film . . . , Journal of Applied Physics, vol. 73, No. 11, p. 7035 (1993).

Fu et al., Optimizing GaN photocathode structure for higher . . . ; Optik, vol. 123, No. 9, May 2012, pp. 756-768.

Hecht, Optics, Fourth Edition, India: Pearson Education Pte, Ltd. 2004.

Hecht, Optics, Second Edition, Adelphi University, 1987, Addison-Wesley Publishing Company, Inc., 3 pages.

Henderson, Brian S., Study of Negative Electron Affinity . . . , Dept. of Physics, Rice Univ., Aug. 7, 2009, 18 pgs.

Howorth et al., Transmission silicon photoemitters . . . , Jrnl of Physics D: Applied Physics, vol. 9, No. 5, Apr. 1, 1976, pp. 785-794.

Huang et al., Back-Side Illuminated Photogate CMOS . . . , IEEE Sensors Journal, vol. 11, No. 9, Sep. 2011, 5 pgs.

ISR and Written Opinion dated Mar. 31, 2014 for PCT/US2013/074124.

Itzler et al., InP-based Geiger-mode . . . , Proc. SPIE vol. 7320 (2000), 12 pgs.

Janesick, James R., Scientific Charge-Coupled Devices, SPIE Press, 2001, pp. 556-561.

KLA-Tencor Coporation, filed U.S. Appl. No. 62/059,368, filed Oct. 3, 2014 and entitled "183nm Laser and Inspection System".

Leng et al, Simultaneous Measurement of Six Layers . . . , Journal of Applied Physics, vol. 81, No. 8, p. 3570 (1997).

Lim, Seunghuyn, Low-Power Analog-to-Digital Converters for . . . ; Graduate School, Yonsei Univ. Dept. of EEE, Feb. 2010, pp. 16-21.

Martinelli, Ramon U., Infrared Photoemission from Silicon, Applied Physics Letters, vol. 16, No. 7, Apr. 1, 1970, pp. 261-262.

Martinelli, Ramon U., Reflection and Transmission Secondary Emission . . . , Applied Physics Letters, vol. 17, No. 8, Oct. 15, 1970, pp. 313-314.

Mouchart et al., Thin Film Optical Coatings. 7: Two Layer Coatings Close to Antireflection, Applied Optics, vol. 18, No. 8, Apr. 15, 1979, pp. 1226-1232.

Nanver et al., Pure-Boron Chemical-Vapor-Deposited Layers: a New Material for Silicon Device Processing, 18th IEEE International Conference on Advanced Thermal Processing of Semiconductors (RTP), Sep. 28, 2010-Oct. 1, 2010, pp. 136-139.

Nanver, Silicon Photodiodes for Low Penetration Depth Beams such as DUV/VUV/EUV Light and Low-Energy Electrons, Advances in Photodiodes, G. Betta, ed., Mar. 22, 2011, pp. 205-224, www.intechopen.com.

Niclass et al., Design and Characterization of a CMOS 3-D . . . , IEEE Journal Solid-State Circuits, vol. 40, No. 9, Sep. 2005, 8 pgs.

Nikzad, Shouleh et al., Delta-doped CCDs High QE with long-term stability . . . ; SPIE vol. 2198 (1994) pp. 907-915.

Paetzel et al., Activation of Silicon Wafer by Excimer Laser, 18th IEEE Conf. Advanced Thermal Processing of Semiconductors-RTP 2010, 5 pgs.

Raoult, Efficient generation of narrow-bandwidth . . . , Jul. 15, 1998, vol. 23, No. 14, Optics Letters, pp. 1117-1119.

Sarubbi et al., Chemical Vapor Deposition of α-Boron Layers on Silicon for Controlled Nanometer-Deep p+ n Junction Formation, J. Electron. Mat., vol. 39, No. 2, Feb. 2010, pp. 162-173.

Sarubbi et al., Pure boron-doped photodiodes . . . IEEE, Sep. 15, 2008, pp. 278-281.

Sobieski, Stanley, Intensified Charge Coupled Devices for Ultra Low Light Level Imaging, NASA, Goddard Space Flight Center, SPIE vol. 78 (1976) Low Light Level Devices, pp. 73-77.

Stevanovic et al., A CMOS Image Sensor for High-Speed Imaging, 2000 IEEE int'l. Solid-State Circuits Conf., 3 pgs.

Tobin, Kenneth W., Inspection in Semiconductor Manufacturing, Webster's Encyclopedia of Electrical and Electronic Engineering, vol. 10, pp. 242-262, Wiley & Sons, NY, NY, 1999.

Vaillant, Joel et al., Int'l Conf. on Space Optics, High performance UV antirelection coating for back thinned CCD and CMOS Image sensors, Oct. 4-8, 2010, 4 pgs.

Xiaogian, Fu, Higher Quantum Efficiency by Optimizing . . . 978-1-4244-6644-3/10 IEEE, pp. 234-235.

\* cited by examiner

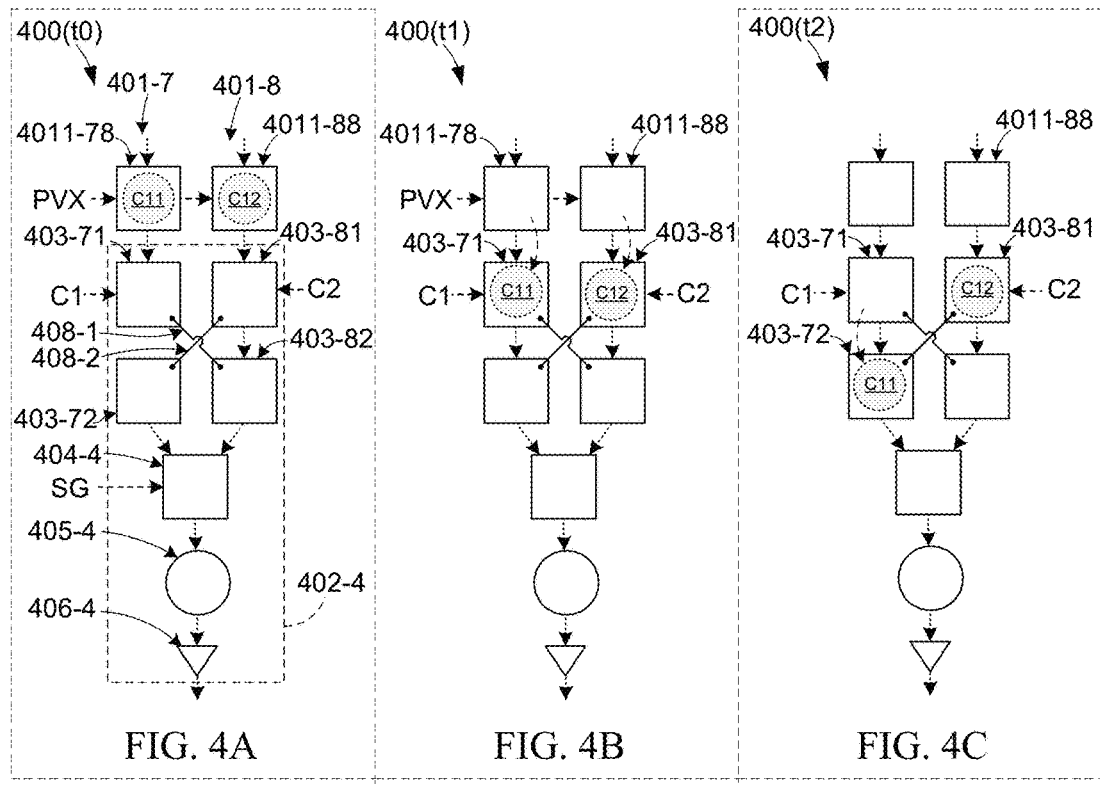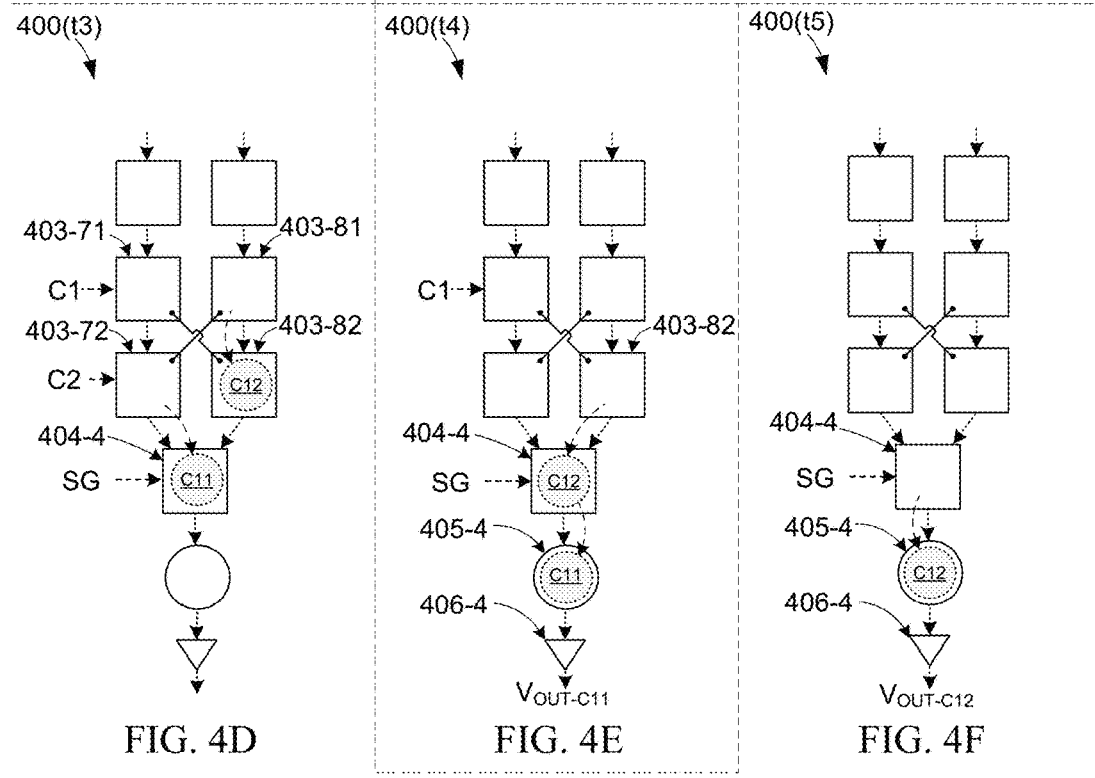

DUAL-COLUMN-PARALLEL CCD SENSOR AND INSPECTION SYSTEMS USING A SENSOR

PRIORITY APPLICATION

The present application claims priority to U.S. Provisional Patent Application 62/319,130 entitled "A DUAL-COLUMN-PARALLEL CCD SENSOR AND INSPECTION SYSTEMS USING A SENSOR", filed by Chuang et al. on Apr. 6, 2016.

BACKGROUND OF THE DISCLOSURE

Field of the Disclosure

The present application relates to image sensors and associated electronic circuits suitable for sensing radiation at visible, UV, deep UV (DUV), vacuum UV (VUV), extreme UV (EUV) and X-ray wavelengths, and for sensing electrons or other charged particles, and to methods for operating such image sensors. The sensors and circuits are particularly suitable for use in inspection systems, including those used to inspect photomasks, reticles, and semiconductor wafers.

Related Art

The integrated circuit industry requires inspection tools that provide increasingly higher sensitivity to detect smaller defects and particles, while maintaining high throughput for a lower cost of ownership. The semiconductor industry is currently manufacturing semiconductor devices with feature dimensions around 20 nm and smaller. Within a few years, the industry will be manufacturing devices with feature dimensions around 5 nm. Particles and defects just a few nm in size can reduce wafer yields and must be captured to ensure high-yield production. Furthermore, efforts have been spent on speeding up inspection to cope with the transition from today's 300 mm wafers to 450 mm wafers in the near future. Thus, the semiconductor industry is driven by ever greater demand for inspection tools that can achieve high sensitivity at high speed.

An image sensor is a key component of a semiconductor inspection tool. It plays an important role in determining defect detection sensitivity and inspection speed. Considering their image quality, light sensitivity, and readout noise performance, CCDs are widely used as image sensors for semiconductor inspection applications. There are two fundamental ways to improve the sensitivity of CCD image sensors. The first one is to increase the amplitude of the signal, and the second one is to reduce the noise level. In the past decades, many efforts have been devoted in both ways. As various technologies, such as backside illumination, anti-reflection coatings, full depletion, and micro-lenses, have been developed, the sensitivity of CCD image sensors has been increased with advancement of quantum efficiency and thereby improvement in signal intensity.

CCD image sensors suffer from three major types of noise, namely shot noise, dark-current noise, and read noise. The photons incident on an image sensor carry time-dependent fluctuations in the photon flux. The image sensor exhibits lower shot noise, the statistical variations in the incident photon flux, when it uses pixel binning and/or frame averaging because then there will be more collected photons per output pixel. Dark current is generated by the thermal excitation of charge carriers into the conduction band within the silicon of an image sensor. CCD cooling, Multi-Pinned-Phase (MPP), and/or dark image subtraction techniques have suppressed the dark-current noise to such a level that its contribution is negligible over the short exposure times (typically a few to hundreds of milliseconds) used in high-speed inspection. Read noise arises from the on-chip electronics and can be reduced by carefully designed electronics and image processing techniques.

As readout speed increases, read noise becomes the dominant noise factor limiting the sensitivity of a CCD image sensor. The CCD on-chip amplifier requires high bandwidth to measure the signal (image) charge in each pixel at a high pixel clock rate. Read noise increases as the result of the high bandwidth. Conventional full-frame CCD image sensors employ a serial-readout architecture, thus demanding a high pixel clock rate (such as 20 MHz or higher) and high readout speed. It is difficult or impossible to reduce the read noise at such high speeds. As pixel sizes on the article being inspected are reduced in order to detect smaller defects (for example, by increasing the optical magnification of the image), increased readout speed is needed to maintain overall inspection speed (e.g. to keep the number of wafers inspected per hour approximately constant as the image pixel size decreases). This means that read noise will tend to increase rather than decrease.

Column-Parallel CCD (CPCCD) image sensors are known in the art. Each column of CPCCD pixels is equipped with an amplifier that facilitates parallel readout of each image charge. See, for example, J. R. Janesick, "Scientific charge-coupled devices", 2001, SPIE, p60. The column-parallel readout eases the requirements for pixel clock rate and can help reduce read noise at high readout speed. However, it is only practical to implement a column-parallel readout architecture for large-pixel CCD designs (such as pixel widths of more than 30 μm). In the case of a CCD sensor with a small column pitch (such as a pitch between about 10 μm and about 25 μm, which is best suited to high-speed semiconductor inspection applications), the one-amplifier-per-column layout cannot be implemented due to space constraints. Furthermore, a column parallel design requires that all outputs be clocked simultaneously. That results in high switching currents and high read noise.

Therefore, a need arises for providing a CCD image sensor that facilitates high-sensitivity and high-speed operation of an inspection system and overcomes some, or all, of the above disadvantages.

SUMMARY OF THE DISCLOSURE

The present invention is directed to dual-column-parallel CCD image sensors and an associated readout method that facilitates both high-sensitivity and high-speed readout operations by way of utilizing a novel readout circuit to coordinate the high-speed transfer of charges generated in associated pairs of adjacent pixel columns to a single (shared) floating diffusion for readout by a single (shared) amplifier. This one-amplifier-per-two-columns arrangement facilitates the production of CCD sensors with small column pitches (e.g., between about 10 μm and about 25 μm) that are suitable for high-speed semiconductor inspection applications by way of avoiding the high switching currents, high read noise, and the amplifier space problems associated with one-amplifier-per-column CPCCD sensors. Moreover, the one-amplifier-per-two-columns arrangement is implemented using an output clock rate that is two-times the line clock rate speed, thereby avoiding both the high pixel clock rate issues associated with conventional CPCCD sensors, and also avoiding the high read noise problems associated with serial readout approaches.

According to an embodiment of the invention, a dual-column-parallel CCD image sensor includes an array of pixels arranged in an even number of columns, and a novel readout circuit includes multiple readout structures respectively coupled to at least one pixel in each of the associated pair of columns. Each readout structure includes two rows of transfer gates operably coupled to receive image charges from the associated pair of columns, a shared summing gate coupled to alternately receive image charges passed from the transfer gates, and an output circuit including a single amplifier configured to generate output voltage signals based on the image charges transferred from the associated pair of columns. According to an aspect of the present invention, the two rows of transfer gates in each pair of associated columns are effectively cross-coupled such that a (first) transfer gate control signal applied to the first-row (first) transfer gate in one column is substantially simultaneously applied to to the second row (fourth) transfer gate in the associated second column, and such that a second transfer gate control signal applied to the first-row (second) transfer gate in the second column is substantially simultaneously applied to the second-row (third) transfer gate in the first column. According to another aspect, the summing gate of each readout structure is configured to receive image charges from the two second-row (third and fourth) transfer gates during different time periods, and is configured to pass each received image charge to an output circuit (e.g., a floating diffusion coupled to an amplifier) in accordance with a summing gate control signal. Cross-coupling the transfer gates in adjacent columns and utilizing a shared summing gate in this manner facilitates efficient and reliable transfer of image charges from two columns of pixels to one shared output circuit with low noise and at a reasonable clock rate (i.e., two times the line clock rate), thereby facilitating the production of image sensors particularly suitable for use in inspection systems, including those used to inspect photomasks, reticles, and semiconductor wafers.

According to another embodiment, an image sensor is fabricated on a semiconductor substrate (e.g. monocrystalline silicon) having formed therein multiple symmetrical Y-shaped buried diffusions, each having parallel upstream (first and second) elongated portions, a downstream (third) elongated portion in which the sense node (i.e., floating diffusion) is formed, and an intervening (fourth) V-shaped merge section connecting the two upstream elongated portions to the downstream elongated portion. The upstream elongated portions respectively define the associated columns mentioned above. Polycrystalline silicon pixel gate structures are formed over the upstream elongated portions, thereby forming pixels that serve to generate image charges and transfer the image charges along the two associated channels toward the V-shaped merge section. Two rows of transfer gates are generated by polycrystalline silicon transfer gate structures formed over portions of the upstream (first and second) elongated portions, with two (first and third) transfer gates configured to transfer image charges from one channel to the V-shaped merge section, and two (second and fourth) transfer gates configured to pass image charges from the associated second channel to the V-shaped merge section. A summing gate is formed by way of a polycrystalline silicon gate structure disposed over the V-shaped merge section and configured to receive image charges from either of the two associated channels by way of the two upstream (first and second) elongated portions, and configured to pass the receive image charges to the downstream elongated section. As in the embodiment described above, the transfer gate electrodes in the two rows of transfer gates are effectively cross-coupled to facilitate efficient and reliable transfer of image charges from the two associated columns to the summing gate, and the summing gate is controlled by a summing gate control signal to pass the image charges from the two associated columns to the shared output circuit (sense node) with low noise and at a reasonable clock rate (i.e., two times the line clock rate). By utilizing symmetrical Y-shaped buried diffusions in combination with the cross-coupled transfer gates and summing gates to transfer image charges to an sense node (e.g., a shared floating diffusion disposed in the downstream elongated diffusion portion), the present invention facilitates the highly efficient, high speed and low noise transfer of image charges from two columns of pixels for output using a single amplifier controlled or otherwise operably coupled to the floating diffusion. Since the transfer gates of adjacent columns switch alternately, the clock signals to the transfer gates are approximately balanced and generate minimal substrate currents thus allowing high-speed clocking while maintaining a low noise level. Since each output is connected to only two columns, in contrast to a conventional high-speed CCD that might have 12, 16 or more columns per output, the pixel clock rate in image sensor is only twice the line clock rate instead of 12, 16 or more times the line clock rate. Since noise increases with a higher bandwidth, an image sensor with a lower pixel clock rate can be less noisy than one with higher pixel clock rate.

According to a specific embodiment, cross-coupling of associated polycrystalline silicon transfer gate structures disposed in the two different rows is achieved by conductive (e.g., metal or doped polycrystalline silicon) linking structures connected between the two associated transfer gate structures. That is, a (first) transfer gate structure disposed in the first row of one column is electrically connected by way of a (first) conductive linking structure to a (fourth) transfer gate structure disposed in the second row of the associated second column. This arrangement facilitates reliable control over both associated transfer gate structures by applying the associated transfer gate control signal to the (first) transfer gate structure, whereby the transfer gate control signal is substantially simultaneously applied to the (fourth) transfer gate structure (i.e., by way of transmission over the (first) conductive linking structure). In one embodiment, the conductive linking structure is implemented using polycrystalline silicon, where the two associated transfer gate structures and the conductive linking structure are fabricated as an integral "Z" shaped composite polycrystalline silicon structure This embodiment avoids the extra complexity, cost and potential reduced yield associated with using two layers of metal interconnections, or alternatively allows a second layer of metal to be used to reduce the series resistance of the clock signals enabling higher speed operation.

According to another specific embodiment, the summing gate is implemented using a tapered polycrystalline silicon structure having an upstream edge (i.e., the edge facing the upstream elongated diffusion portions) that is longer than its downstream edge (i.e., the edge facing the downstream elongated diffusion portion). The tapered summing gate structure facilitates efficient transfer of image charges from both upstream elongated diffusion portions to the downstream elongated diffusion portion. In a preferred embodiment, a similarly tapered output gate structure is disposed over a downstream portion of the V-shaped merge section (i.e., between the summing gate structure and the downstream elongated diffusion portion), and functions to prevent charge spill from the sense node back to the summing gate.

According to another specific embodiment, the shared output circuit of each associated column pair includes a floating diffusion formed in the downstream (third) elongated diffusion portion, and an on-chip pre-amplifier that is operably coupled to the floating diffusion by way of a conductive (metal or polycrystalline silicon) structure. In one embodiment, the conductive structure is implemented using a polycrystalline silicon structure that is formed and patterned such that a lower/vertical poly portion extends through a contact hole to the floating diffusion, and an upper/horizontal poly portion extends horizontally from the lower/vertical poly portion and forms the gate structure for a first-stage gain transistor of the on-chip pre-amplifier. This arrangement facilitates self-alignment of the floating diffusion and the polysilicon gate structure, and facilitates connection to the pre-amplifier without the need for a metal interconnect, thereby further reducing noise and floating diffusion capacitance and increasing charge conversion efficiency, thus improving the sensor's signal-to-noise ratio.

An inspection method utilizing the dual-column-parallel CCD sensor of the present invention includes directing and focusing radiation onto the sample, and receiving radiation from the sample and directing received radiation to a CCD image sensor. The received radiation may include scattered radiation or reflected radiation. The CCD sensor incorporates a dual-column-parallel readout structure comprising two pairs of transfer gates, a common summing gate, a floating diffusion (also known as a sense node), and an amplifier per two columns. The dual-column-parallel readout structure is implemented in a way that all the columns have identical charge transfer and signal readout paths. In one embodiment, the dual-column-parallel CCD may use a self-aligned floating diffusion with a polysilicon contact connected to the amplifier. In another embodiment the dual-column-parallel CCD may comprise metal interconnects in the readout structure with equalized channel response and minimized crosstalk.

The method of inspecting can further include generating clock voltage waveforms and controlling the timing of the on-chip dual-column-parallel readouts and the off-chip signal processing circuits for appropriate synchronization of the sensor readout and digitization of the output signals. Three exemplary embodiments of clock voltage waveforms and timing configurations to drive the on-chip dual-column-parallel readouts and the off-chip signal processing circuits are described. These are merely by way of example to explain some of the possible methods for synchronization of the sensor output. The above clock driving schemes may be implemented by an apparatus including an analog-to-analog converter (ADC), a digital signal processor, a clock driver, and external processing, storage, and control circuitry.

A system for inspecting a sample is also described. This system includes an illumination source, a light detection device, optics configured to direct light from the illumination source to the sample and to direct light outputs or reflections from the sample to the device, and a driving circuit. In one embodiment, the light detection device may comprise a CCD array sensor, such as a Time Delay Integration (TDI) sensor. In another embodiment, the device may comprise a CCD line sensor. The CCD sensor incorporates a dual-column-parallel readout structure comprising, per pair of adjacent columns, two pairs of transfer gates, a common summing gate, a floating diffusion, and an amplifier. Each column of the CCD pixels is terminated by a pair of transfer gates. Each pair of adjacent columns combine into a common summing gate, and the common summing gate tapers towards a small floating diffusion where an amplifier converts each image charge to a corresponding output voltage signal. The dual-column-parallel readout structure is implemented in a way that all the columns have substantially identical charge transfer and signal readout path characteristics. The driving circuit supplies bias voltages and clock signals to the on-chip dual-column-parallel readout structure and off-chip signal processing circuits in order to read the sensor output with the desired timing.

In one embodiment, the CCD sensor may further comprise a semiconductor membrane. In another embodiment, the semiconductor membrane may include circuit elements formed on a first surface of the semiconductor membrane and a pure boron layer deposited on a second surface of the semiconductor membrane. In yet another embodiment, the system may include multiple CCD sensors.

The sample may be supported by a stage, which moves relative to the optics during the inspection. The electrical charges may be read out from the sensor in synchrony with the motion of the stage.

The exemplary inspection system may include one or more illumination paths that illuminate the sample from different angles of incidence and/or different azimuth angles and/or with different wavelengths and/or polarization states. The exemplary inspection system may include one or more collection paths that collect light reflected or scattered by the sample in different directions and/or are sensitive to different wavelengths and/or to different polarization states.

BRIEF DESCRIPTION OF THE DRAWINGS

FIGS. 4A, 4B, 4C, 4D, 4E and 4F illustrate a portion of the exemplary dual-column-parallel CCD sensor of FIG. 4 during operation.

DETAILED DESCRIPTION OF THE DRAWINGS

The present invention relates to an improvement in sensors for semiconductor inspection systems. The following description is presented to enable one of ordinary skill in the art to make and use the invention as provided in the context of a particular application and its requirements. As used herein, directional terms such as "top", "bottom", "over", "under", "underneath", "left", "right", "vertical", "horizontal" and "down" are intended to provide relative positions for purposes of description, and are not intended to designate an absolute frame of reference. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed.

Figure 1:
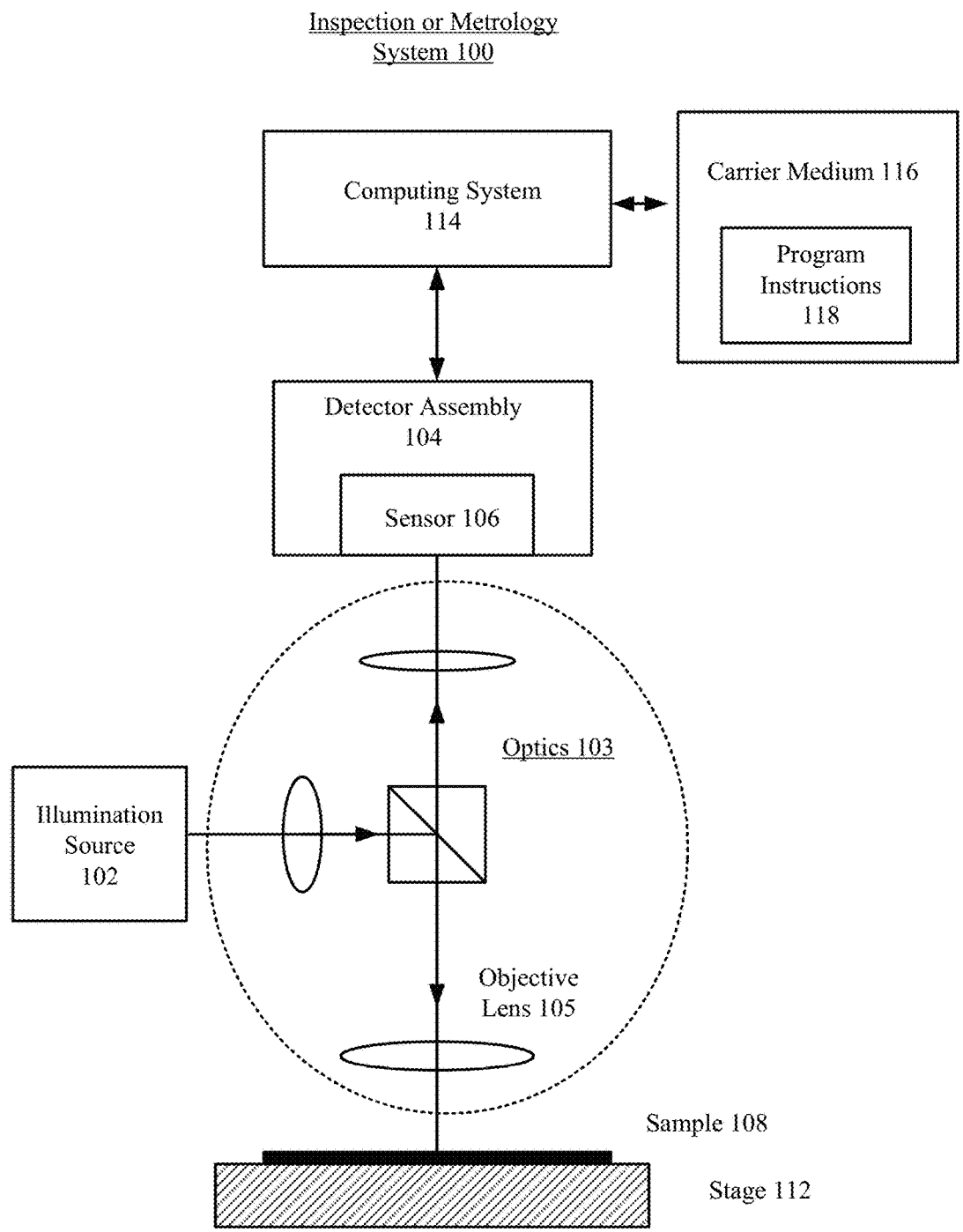
FIG. 1 illustrates an exemplary inspection system.

FIG. 1 illustrates an exemplary inspection system 100 configured to inspect a sample 108, such as a wafer, reticle, or photomask. Sample 108 is placed on a stage 112 to facilitate movement to different regions of sample 108 underneath the optics. Stage 112 may comprise an X-Y stage or an R-θ stage. In some embodiments, stage 112 can adjust the height of sample 108 during inspection to maintain focus. In other embodiments, an objective lens 105 can be adjusted to maintain focus.

An illumination source 102 may comprise one or more lasers and/or a broad-band light source. Illumination source 102 may emit DUV and/or VUV radiation. Optics 103, including an objective lens 105, directs that radiation towards and focuses it on sample 108. Optics 103 may also comprise mirrors, lenses, polarizers and/or beam splitters (not shown for simplicity). Light reflected or scattered from sample 108 is collected, directed, and focused by optics 103 onto a sensor 106, which is within a detector assembly 104.

Detector assembly 104 includes at least one of the sensors described herein. In one embodiment, the output of sensor 106 is provided to a computing system 114, which analyzes the output. Computing system 114 is configured by program instructions 118, which can be stored on a carrier medium 116. In one embodiment computing system 114 controls the inspection system 100 and sensor 106 to inspect a structure on sample 108 and read out the sensor in accordance with a method disclosed herein.

In one embodiment, illumination source 102 may be a continuous source, such as an arc lamp, a laser-pumped plasma light source, or a CW laser. In another embodiment, illumination source 102 may be a pulsed source, such as a mode-locked laser, a Q-switched laser, or a plasma light source pumped by a Q-switched laser. In one embodiment of inspection system 100 incorporating a Q-switched laser, the sensor or sensors within detector assembly 104 are synchronized with the laser pulses.

One embodiment of inspection system 100 illuminates a line on sample 108, and collects scattered and/or reflected light in one or more dark-field and/or bright-field collection channels. In this embodiment, detector assembly 104 may include a line sensor or an electron-bombarded line sensor. Another embodiment of inspection system 100 illuminates an area on sample 108, and collects scattered and/or reflected light in one or more dark-field and/or bright-field collection channels. In this embodiment, detector assembly 104 may include an array sensor or an electron-bombarded array sensor.

Additional details of various embodiments of inspection system 100 are described in U.S. Pat. No. 9,279,774, entitled "Wafer inspection system", issued on Mar. 8, 2016 to Romanovsky et al., U.S. Pat. No. 7,957,066, entitled "Split field inspection system using small catadioptric objectives", to Armstrong et al., U.S. Pat. No. 7,345,825, entitled "Beam delivery system for laser dark-field illumination in a catadioptric optical system", to Chuang et al., U.S. Pat. No. 5,999,310, entitled "Ultra-broadband UV microscope imaging system with wide range zoom capability", issued on Dec. 7, 1999, U.S. Pat. No. 7,525,649, entitled "Surface inspection system using laser line illumination with two dimensional imaging", issued on Apr. 28, 2009. All of these patents are incorporated herein by reference.

Figure 2A:
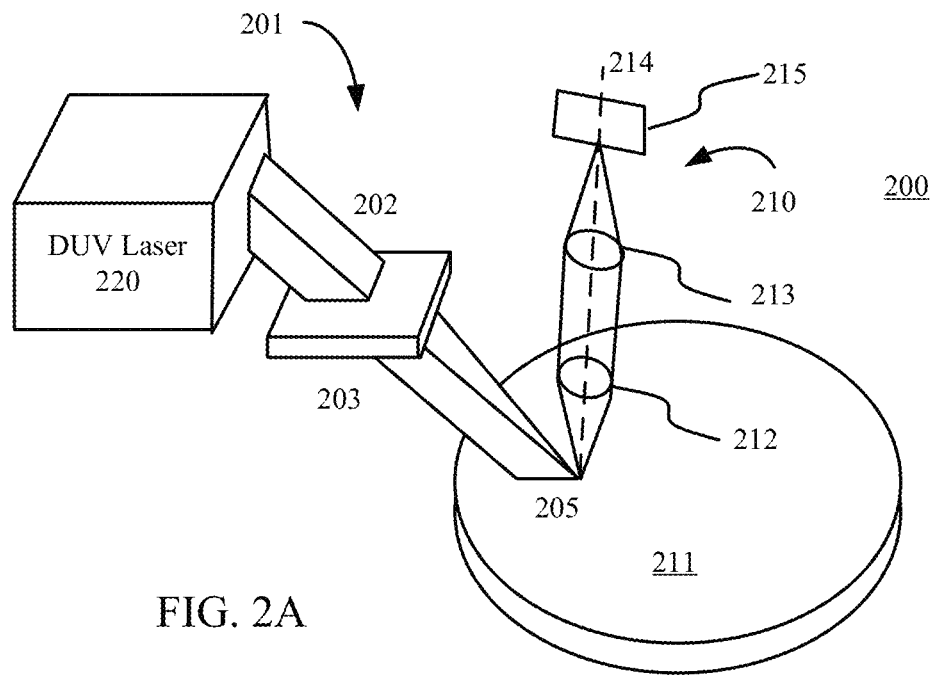
FIGS. 2A and 2B illustrates an exemplary inspection system with line illumination and one or more collection channels.
Figure 2B:
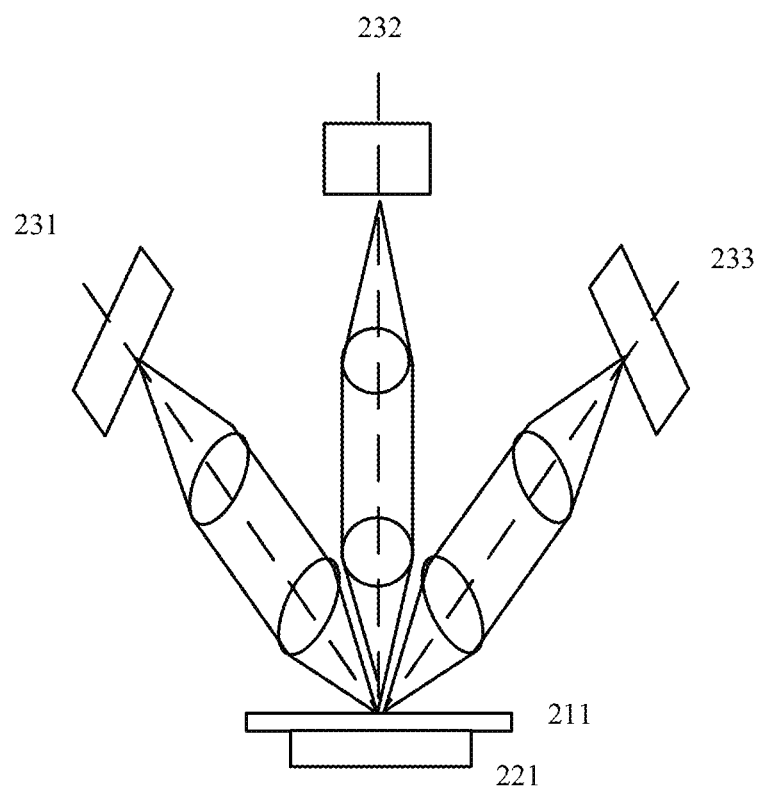

FIGS. 2A and 2B illustrate aspects of dark-field inspection systems that incorporate sensors and/or methods described herein in accordance with other exemplary embodiments of the present invention. In FIG. 2A, illumination optics 201 comprises a laser system 220, which generates light 202 that is focused by a mirror or lens 203 into a line 205 on surface of a wafer or photomask (sample) 211 being inspected. The sample being inspected may be patterned or unpatterned. Collection optics 210 directs light scattered from line 205 to a sensor 215 using lenses and/or mirrors 212 and 213. An optical axis 214 of collection optics 210 is not in the illumination plane of line 205. In some embodiments, optical axis 214 is approximately perpendicular to line 205. Sensor 215 comprises an array sensor, such as a linear array sensor. Sensor 215 may comprise a sensor as described herein, and/or one of the methods described herein may be used to read out the sensor.

FIG. 2B illustrates one embodiment of multiple dark-field collection systems 231, 232 and 233, each collection system substantially similar to collection optics 210 of FIG. 2A. Collection systems 231, 232 and 233 may be used in combination with illumination optics substantially similar to illumination optics 201 of FIG. 2A. Each collection system 231, 232 and 233 incorporates one, or more, of the sensors described herein. Sample 211 is supported on stage 221, which moves the areas to be inspected underneath the optics. Stage 221 may comprise an X-Y stage or an R-θ stage, which preferably moves substantially continuously during the inspection to inspect large areas of the sample with minimal dead time.

More details of inspection systems in accordance with the embodiments illustrated in FIGS. 2A and 2B are described in U.S. patent application Ser. No. 15/153,542 entitled "Sensor With Electrically Controllable Aperture For Inspection And Metrology Systems", filed May 12, 2016, U.S. Pat. No. 7,525,649, entitled "Surface inspection system using laser line illumination with two dimensional imaging", issued on Apr. 28, 2009, and U.S. Pat. No. 6,608,676, entitled "System for detecting anomalies and/or features of a surface", issued on Aug. 19, 2003. All of these patents and patent applications are incorporated herein by reference.

Figure 3:
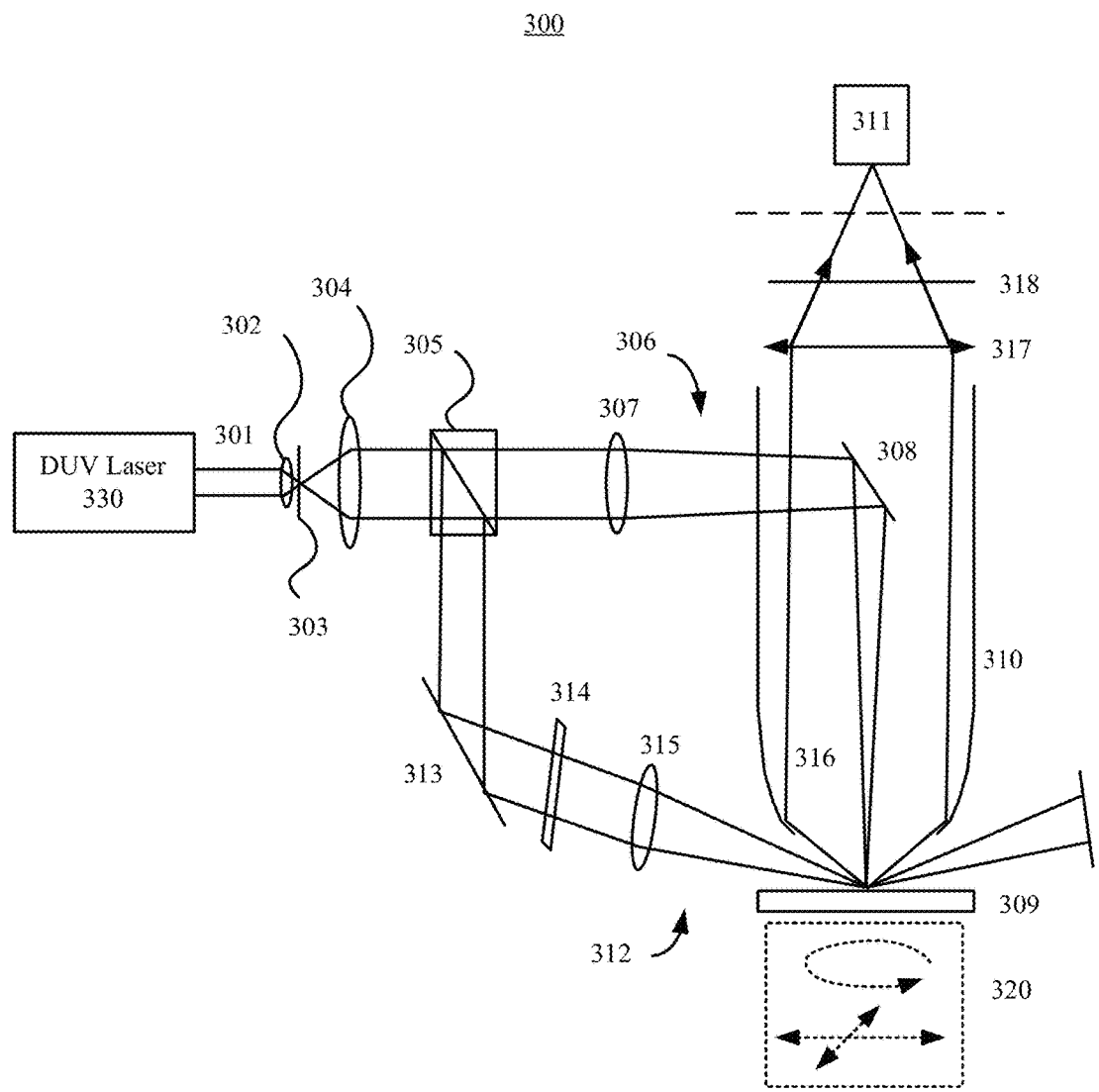
FIG. 3 illustrates an exemplary inspection system with normal and oblique illumination.

FIG. 3 illustrates an inspection system 300 configured to detect particles or defects on a sample, such as an unpatterned wafer, using both normal and oblique illumination beams. In this configuration, a laser system 330 provides a laser beam 301. A lens 302 focuses beam 301 through a spatial filter 303. Lens 304 collimates the beam and conveys it to a polarizing beam splitter 305. Beam splitter 305 passes a first polarized component to the normal illumination channel and a second polarized component to the oblique illumination channel, where the first and second components are orthogonal. In a normal illumination channel 306, the first polarized component is focused by optics 307 and reflected by a mirror 308 towards a surface of a sample 309. The radiation scattered by sample 309 (such as a wafer or photomask) is collected and focused by a paraboloidal mirror 310 to a sensor 311.

In an oblique illumination channel 312, the second polarized component is reflected by a beam splitter 305 to a mirror 313 which reflects such beam through a half-wave plate 314 and focused by optics 315 to sample 309. Radiation originating from the oblique illumination beam in oblique channel 312 and scattered by sample 309 is collected by paraboloidal mirror 310 and focused to sensor 311. Sensor 311 and the illuminated area (from the normal and oblique illumination channels on sample 309) are preferably at the foci of paraboloidal mirror 310.

Paraboloidal mirror 310 collimates the scattered radiation from sample 309 into a collimated beam 316. Collimated beam 316 is then focused by an objective 317 and through an analyzer 318 to sensor 311. Note that curved mirrored surfaces having shapes other than paraboloidal shapes may also be used. An instrument 320 can provide relative motion between the beams and sample 309 so that spots are scanned across the surface of sample 309. Sensor 311 may comprise one or more of the sensors described herein. U.S. Pat. No. 6,201,601, entitled "Sample inspection system", issued to Vaez-Iravani et al. on Mar. 13, 2001, U.S. Pat. No. 9,279,774, entitled "Wafer Inspection", issued to Romanovsky et al. on Mar. 8, 2016, and U.S. Published Application 2016-0097727, entitled "TDI Sensor in a Darkfield System" by Vazhaeparambil et al. and published on Apr. 7, 2016, describe additional aspects and details of inspection system 300. These documents are incorporated herein by reference.

Figure 4:
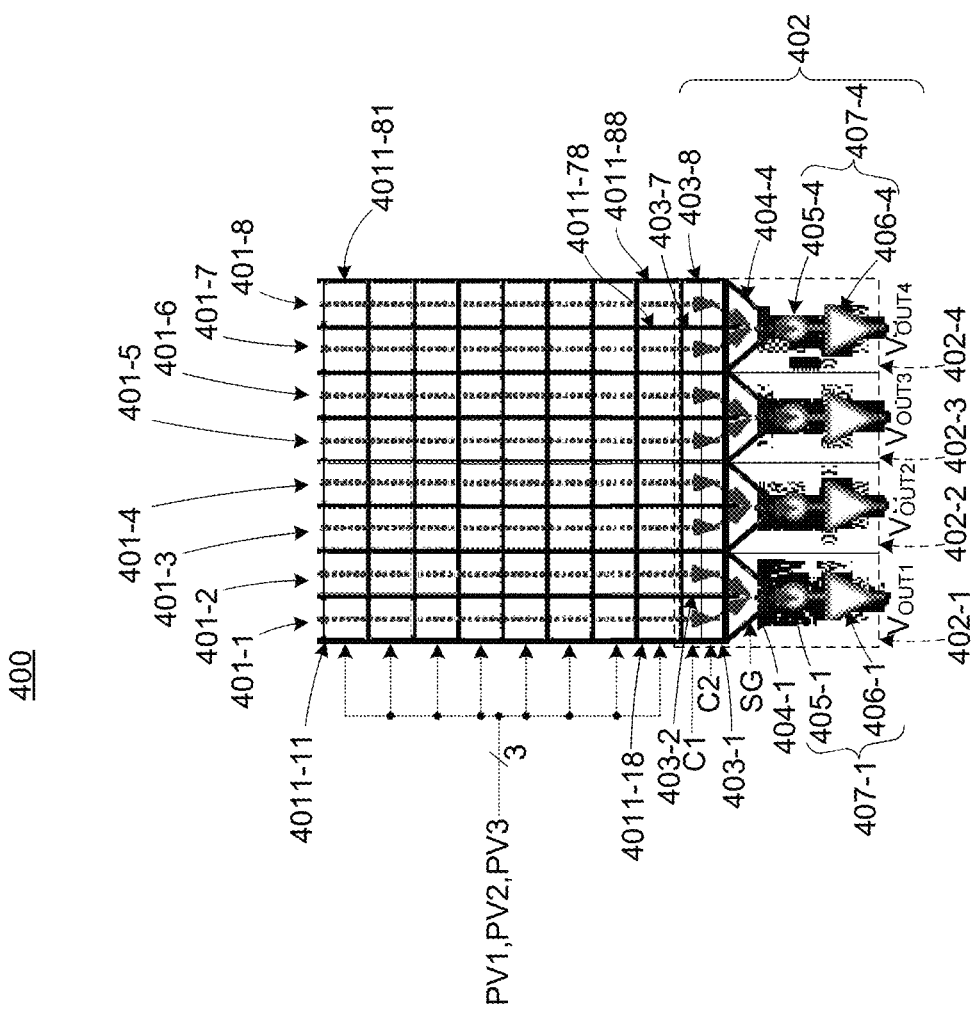
FIG. 4 illustrates an exemplary dual-column-parallel CCD sensor.

FIG. 4 illustrates an exemplary dual-column-parallel CCD sensor 400 in accordance with certain embodiments of the present invention. Sensor 400 comprises an even number of columns 401-1 through 401-8. In a preferred embodiment sensor 400 comprises between about 50 and about 10,000 columns. Each column 401-1 to 401-8 comprises an equal number of square or rectangular pixels (e.g., column 401-1 includes eight pixels 4011-11 to 4011-18 and column 401-8 includes eight pixels 4011-81 to 4011-88). In a preferred embodiment, sensor 400 is an array dual-column-parallel CCD, wherein each column comprises between about 50 and about 10,000 pixels. The numbers of pixels in each column of the array may, or may not, be equal to the number of columns. In an alternative embodiment (not shown), the sensor could be a line dual-column-parallel CCD, wherein each column comprises a single pixel. The line sensor may incorporate a resistive gate similar to one described in U.S. Published Application 2011-0073982, entitled "Inspection System Using Back Side Illuminated Linear Sensor" published Mar. 31, 2011, and filed by Armstrong et al., or similar to one described in the above cited U.S. patent application Ser. No. 15/153,543, which are incorporated herein by reference. Light, radiation or charged particles are incident on sensor 400, causing the generation of image charges in each pixel. The image charges move down the columns of pixels by way of three-phase line control (clock) signals PV1, PV2 and PV3 that are applied to the pixels in the manner described below (PV1, PV2 and PV3 may also be referred to as vertical clock signals). For example, an image charge generated in pixel 4011-81 moves downward to pixel 4011-82 in response to control signals PV1-PV3, and subsequently from pixel to pixel downward along column 401-8 until it reaches pixel 4011-88. In an alternative embodiment, two-phase line control signals may be used instead of three-phase line control signals. An advantage of a sensor configured with three-phase line control signals is that charge may be moved in either direction by appropriate driving signals applied to PV1-PV3, whereas two-phase line control signals can only move the charge in one direction. A sensor using three-phase line control signals may be configured with readout circuits at both the top and bottom of the pixel array to enable readout of the signal in either direction (only readout circuit 402 at the bottom of the array is shown in FIG. 4). Depending on whether single direction or bidirectional transfer is required, sensor 400 may use two-phase or three-phase line control signals.

Referring to the lower portion of FIG. 4, dual-column-parallel CCD sensor 400 also includes a readout (output) circuit 402 that functions to convert the image charges transferred along columns 401-1 to 401-8 into output voltage signals $V_{OUT1}$ to $V_{OUT4}$. Readout circuit 402 includes multiple readout structures 402-1 to 402-4 that respectively receive image charges from an associated pair of adjacent columns 401-1 to 401-8, whereby image charges passed along each column are converted to output voltage signals by a readout structure that is shared with an adjacent associated column. For example, image charges passed along column 401-1 and associated column 401-2 are converted to output voltage signals $V_{OUT1}$ by readout structure 402-1. Similarly, readout structure 402-2 converts image charges received from associated columns 401-3 and 401-4 to generate output voltage signals $V_{OUT2}$, readout structure 402-3 converts image charges received from associated columns 401-5 and 401-6 to generate output voltage signals $V_{OUT3}$, and readout structure 402-4 converts image charges received from associated columns 401-7 and 401-8 to generate output voltage signals $V_{OUT4}$.

Figure 8A:
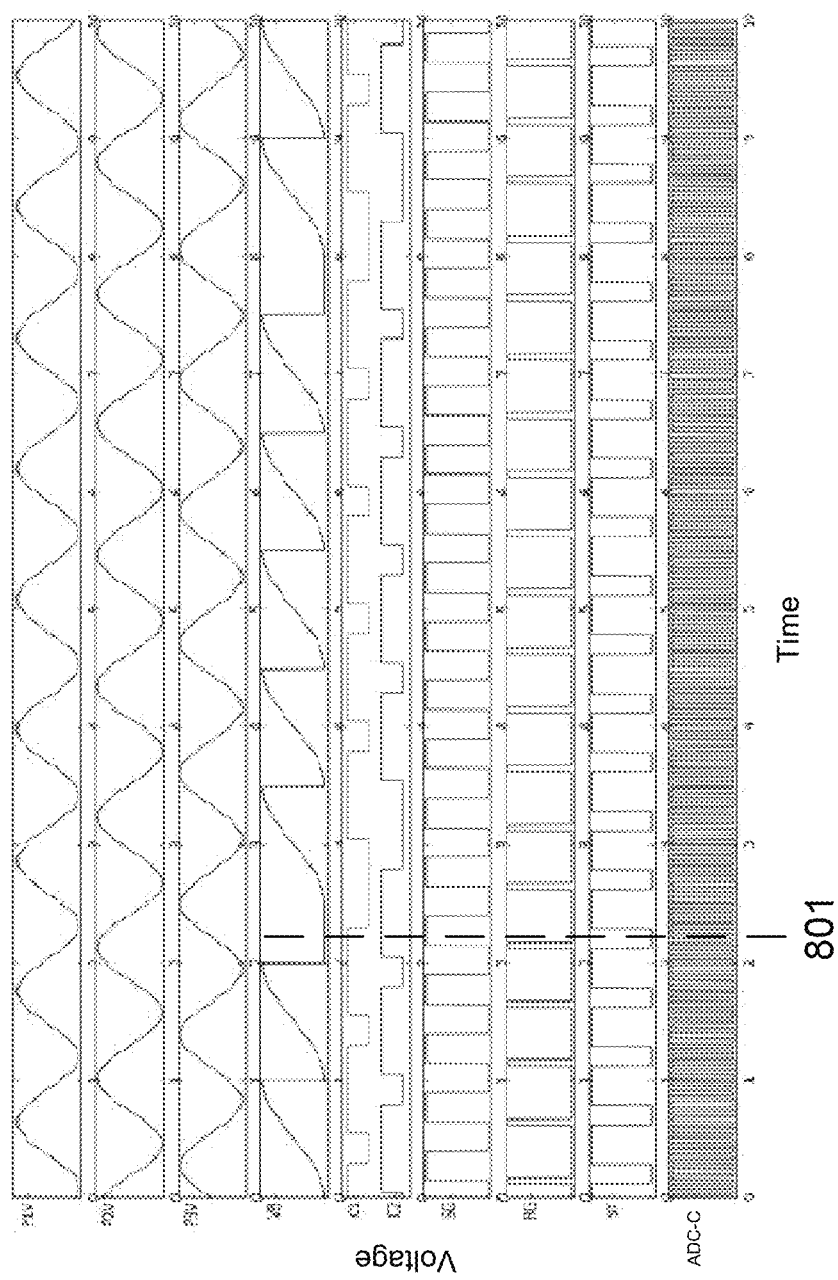
FIGS. 8A, 8B, and 8C illustrate exemplary voltage waveforms and timing configurations of clock signals to drive the on-chip dual-column-parallel readouts and off-chip signal processing circuits in accordance with embodiments of the present invention.
Figure 8B:
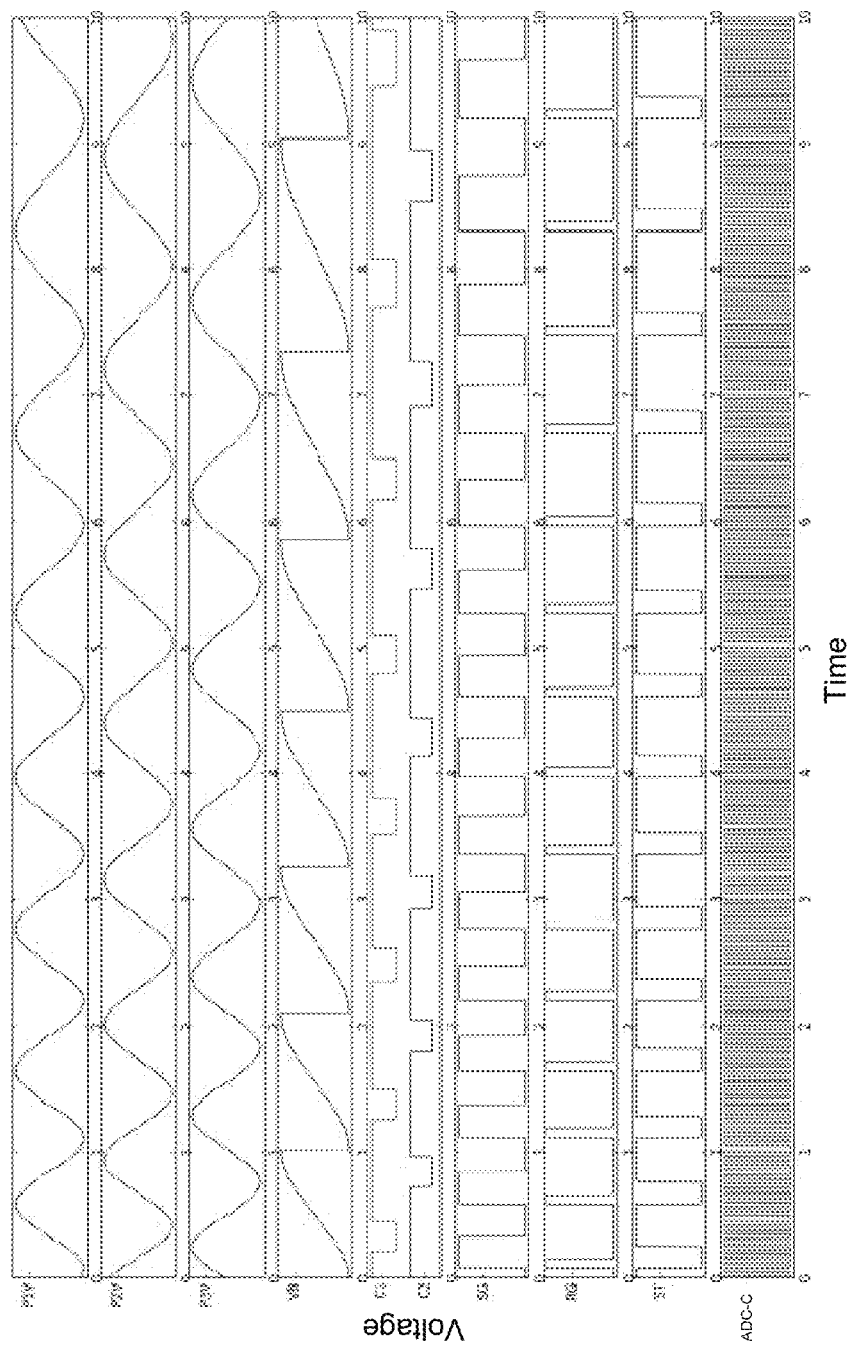
Figure 8C:
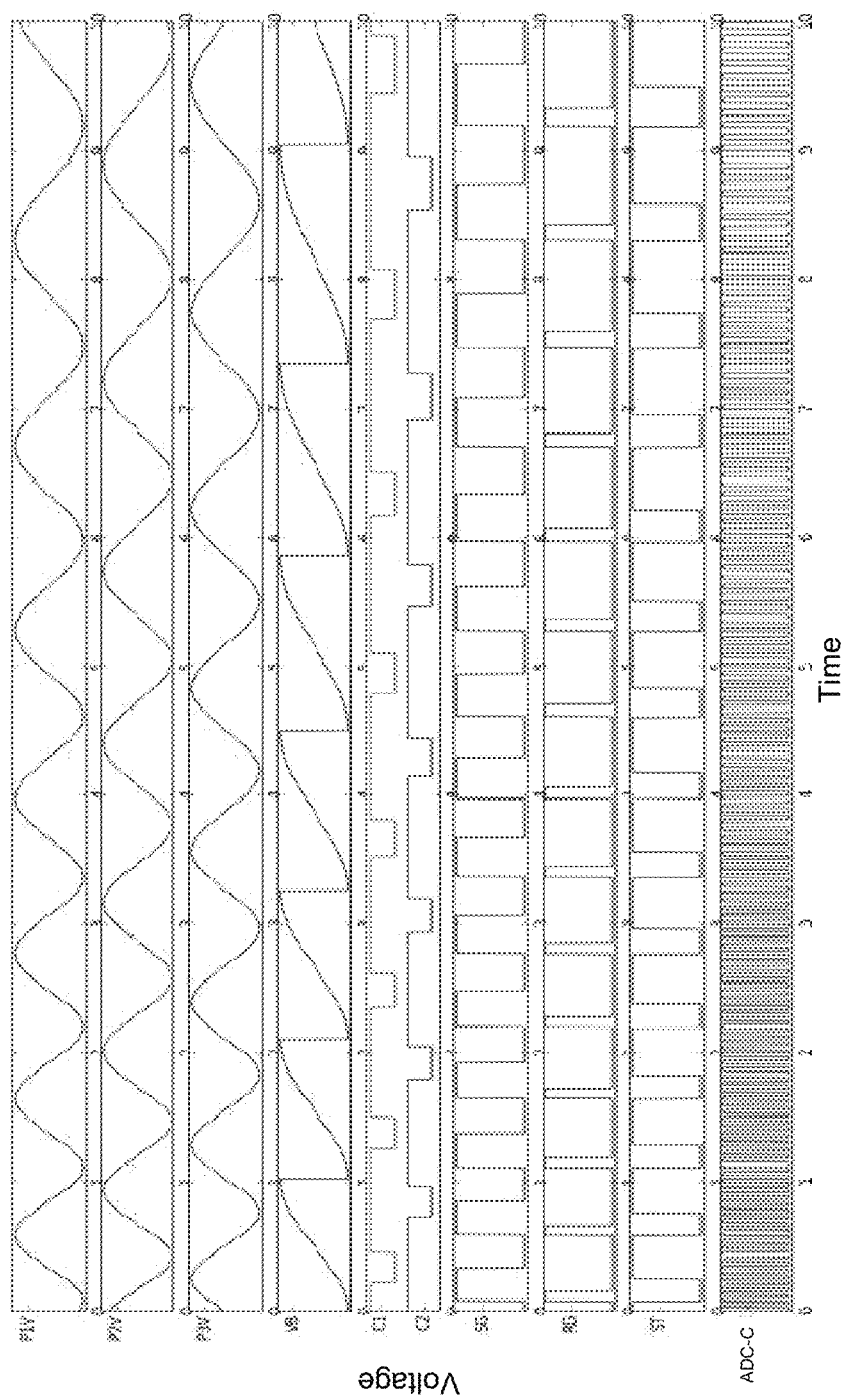

Each readout structure 402-1 to 402-4 includes two pairs of transfer gates configured to transfer respective image signals to a shared summing gate in accordance with transfer gate control signals C1 and C2, which in turn passes the image signals to an associated sense node in accordance with a summing gate control signal SG. For example, readout structure 402-1 includes a first pair of transfer gates 403-1 disposed in column 401-1 and a second pair of transfer gates 403-2 disposed in column 401-2, where transfer gate pairs 403-1 and 403-2 are controlled to pass respective image signals from columns 401-1 and 401-2 to shared summing gate 404-1, and summing gate 404-1 is configured to pass the image signals to an output circuit 407-1, which in one example includes a floating diffusion (sense node) 405-1 and an amplifier 406-1. Similarly, readout structure 402-4 includes transfer gate pairs 403-7 and 403-8 disposed to pass respective image signals from columns 401-7 and 401-8 to shared summing gate 404-4 for transmission from output circuit 407-4 (e.g., floating diffusion 405-4 and amplifier 406-4). As image charge moves down column 401-7, transfer gate pair 403-7 controls the transfer of the image charge from pixel 4011-78 into the common summing gate 404-4, and prevents the spill of the image charge back into pixel 4011-78. Transfer gate pair 403-8 performs a similar function for column 401-8 and the last pixel in that column 4011-88. Summing gate 404-4 accumulates image charge without adding noise during charge transfer. At the bottom of common summing gate 404-4, a small floating diffusion 405-4 is formed to collect and stores image charge transferred from the common summing gate. Transfer gate pairs 403-7 and 403-8 and common summing gate 404-5 are controlled by clock/control signals C1, C2 and SG so that image charge from two adjacent columns is sequentially clocked out into floating diffusion 405-4. Voltage waveforms and timing configurations of the above clock signals are depicted in FIGS. 8A, 8B, and 8C. Floating diffusion 405-4 is attached to a shared amplifier 406-4, which converts image charge to voltage and transmits buffered voltage to an off-chip ADC (not shown). Details of amplifier 406-4 are explained below.

FIGS. 4A to 4F depict a portion of dual-column-parallel CCD sensor 400 showing readout structure 402-4 in additional detail, and also depict the transfer of two image charges C11 and C12 from columns 401-7 and 401-8 to readout structure 402-4 during exemplary simplified operation of sensor 400. In these figures the operating state of sensor 400 is depicted at six sequential time periods t0 to t5, which are indicated in parentheses at the top of each figure (e.g., FIG. 4A shows sensor 400 during an initial time period t0, indicated by "400(t0)"). To simplify the following description, only the position of image charges C11 and C12 is depicted in FIGS. 4A to 4F, and other image charges concurrently being processed by the circuit elements during time t0 to t5 are omitted for clarity. The operation of readout structures 402-1 to 402-3 (FIG. 4) is understood to be essentially identical to that described below.

FIG. 4A shows sensor 400(t0) when (first and second) image charges are respectively stored in pixels 4011-78 and 4011-88 prior to being passed into readout structure 402-4. Pixels 4011-78 and 4011-88 are respectively configured to generate (i.e., collect and/or temporarily store) image charges C11 and C12, and to subsequently pass image charges C11 and C12 to readout structure 402-4 in accordance with one or more line control signals PVX (e.g., three-phase signals PV1, PV2 and PV3 shown in FIG. 4). Readout structure 402-4 includes first-row transfer gates 403-71 and 403-81 that are configured to receive (i.e., either directly or by way of one or more intervening buffer gates, not shown) image charges C11 and C12 from pixels 4011-78 and 88, respectively, second-row transfer gates 403-72 and 403-82 configured to receive image charges C11 and C12 from transfer gates 403-71 and 403-81, respectively, a summing gate 404-4 coupled to transfer gates 403-72 and 403-82, and an output circuit (e.g., a floating diffusion 405-4 and amplifier 406-4) coupled to summing gate 404-4. Note that first and third transfer gates 403-71 and 403-72 form transfer gate pair 403-7 (see FIG. 4), and second and fourth transfer gates 403-81 and 403-82 form transfer gate pair 403-8 (FIG. 4), and that a signal path between the transfer gates of each pair is configured such that image charges C11 and C12 are constrained to travel only in columns 401-7 (i.e., from transfer gate 403-71 to 403-72) and 401-8 (i.e., from transfer gate 403-81 to 403-82), respectively.

As indicated in FIG. 4A, according to an aspect of the present invention, first-row transfer gates 403-71 and 403-81 are effectively cross-coupled with second-row transfer gates 403-72 and 403-82 (e.g., as indicated by conductor 408-1 connected between transfer gates 403-71 and 403-82, and by conductor 408-2 connected between transfer gates 403-72 and 403-81. With this arrangement, a (first) transfer gate control signal C1 applied to (first) transfer gate 403-71 is also substantially simultaneously applied to (fourth) transfer gate 403-82, and a (second) transfer gate control signal C2 applied to (second) transfer gate 403-81 is substantially simultaneously applied to (third) transfer gate 403-72. As explained below, effectively cross-coupling the transfer gates in adjacent columns in this manner facilitates reliable transfer of image charges to a single output circuit (e.g., by way of summing gate 404-4) during alternating time periods, thereby facilitating the output of image charges generated in two columns 401-7 and 401-8 by way of a single amplifier 406-4.

According to another aspect of the present invention, summing gate 404-4 is configured to receive image charges from second-row (third and fourth) transfer gates 403-72 and 403-82 during different time periods, and is configured to pass each received image charge to floating diffusion 405-4 in accordance with summing gate control signal SG. As described below, the cross-coupling of transfer gate 403-71 with transfer gate 403-82 and the cross-coupling of transfer gate 403-72 with transfer gate 403-81 reliably assures that only one image charge is transferred to summing gate 404-4 at a time, thereby facilitating the simplified reliable transfer of image charges from two columns 401-7 and 401-8 to a single floating diffusion 405-4, which is operably coupled to generate an associated output signal by way of amplifier 406-4. To facilitate outputting image charge from two columns 401-7 and 401-8, summing gate control signal SG is provided at a clock rate that is two-times the line clock rate of line control signal(s) PVX.

FIGS. 4B and 4C depict sensor 400 at time periods t1 and t2 during the alternating (sequential) transfer of image charges C11 and C12 into the transfer gates from pixels 4011-78 and 4011-88 according to a simplified exemplary embodiment. During time period t1 (FIG. 4B), the line control signals PVX and transfer gate control signal C1 are actuated/toggled to cause the transfer of image charge C11 from pixel 4011-78 into first transfer gate 403-71, and the transfer of image charge C12 from pixel 4011-88 into second transfer gate 403-81. During time period t2 (FIG. 4C), transfer gate control signals C1 and C2 are actuated to cause the transfer of image charge C11 from first transfer gate 403-71 into third transfer gate 403-72.

FIGS. 4D and 4E depict sensor 400 during time periods t3 and t4 during the subsequent sequential transfer of image charges C11 and C12 from second-row transfer gates 403-72 and 403-82 into summing gate 404-4. During (first) time period t3 (FIG. 4D), (first) transfer gate control signal C1, (second) transfer gate control signal C2, and summing gate control signal SG are actuated/toggled to cause image charge C11 to transfer from second-row transfer gate 403-72 into summing gate 404-4, and to simultaneously cause image charge C12 to transfer from first-row transfer gate 403-81 into second-row (fourth) transfer gate 403-82. Note that the two charge transfers depicted in FIG. 4D are operably beneficially coordinated in response to the actuation/toggling of transfer gate control signals C1 and C2 due to the effective cross-coupling of transfer gates 403-71 and 403-82, and of transfer gates 403-81 and 403-72. During (second) time period t4 (FIG. 4E), (first) transfer gate control signal C1 and summing gate control signal SG are actuated/toggled to cause image charge C12 to transfer from second-row transfer gate 403-82 into summing gate 404-4.

FIGS. 4E and 4F depict sensor 400 during time periods t4 and t5 during the sequential transfer of image charges C11 and C12 from summing gate 404-4 into floating diffusion 405-4. As indicated in FIG. 4E, during (second) time period t4, summing gate 404-4 is controlled by way of summing gate control signal SG to transfer image charge C11 to floating diffusion 405-4, whereby the associated charge stored on floating diffusion 405-4 causes amplifier 406-4 to generate an output voltage signal $V_{OUT-C11}$ corresponding to image charge C11. During subsequent time period t5 (FIG. 4F), summing gate 404-4 is controlled by summing gate control signal SG to transfer image charge C11 into floating gate 405-4, whereby the associated charge stored on floating diffusion 405-4 causes amplifier 406-4 to generate an output voltage signal $V_{OUT-C12}$ corresponding to image charge C12. Note that floating diffusion 405-4 may be reset between each charge transfer (i.e. after transfer of C11 before transfer of C12), or may be reset only before transfer of C11. The reset transistor and the reset signal are not depicted in FIGS. 4, 4A-F in order to simplify the figures and explain the charge transfer operation more clearly.

As established by the example shown in FIGS. 4A to 4F, sensor 400 provides a one-amplifier-per-two-columns arrangement that facilitates the production of CCD sensor with small column pitches (e.g., between about 10 µm and about 25 µm) by way of avoiding the high switching currents, high read noise, and the amplifier space problems associated with one-amplifier-per-column approaches, while only marginally increasing output clock rates (i.e., summing gate control signal SG has a clock rate that is only twice the line clock rate of line control signal(s) PVX).

Figure 5:
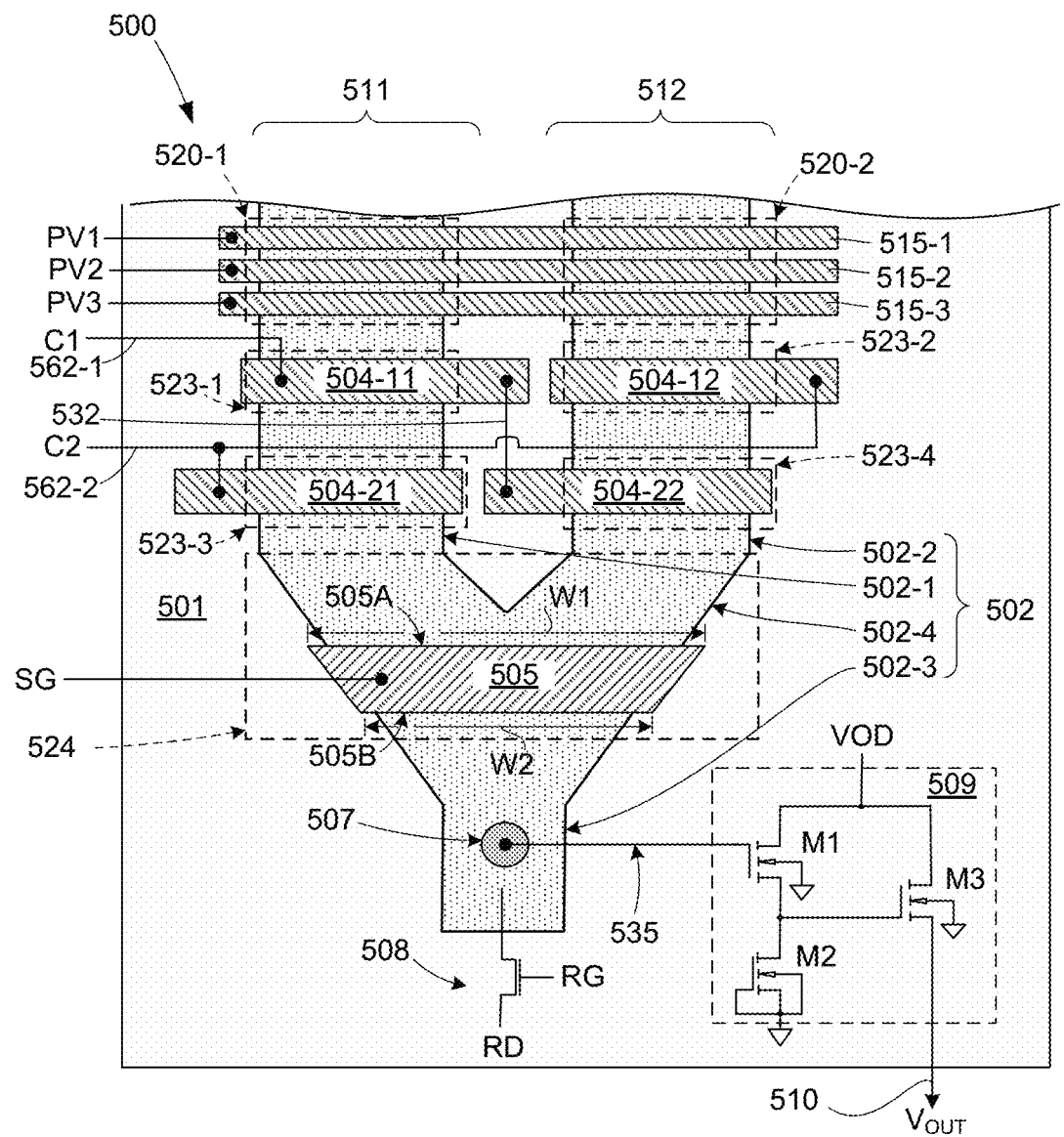
FIG. 5 illustrates a partial dual-column-parallel CCD sensor including a readout structure fabricated in accordance with another exemplary embodiment of the present invention.

FIG. 5 illustrates a partial dual-column-parallel CCD image sensor 500 according to an exemplary preferred embodiment of the present invention.

According to an aspect of the present invention, sensor 500 includes a symmetrical Y-shaped buried diffusion 502 that serves to facilitate the transfer of image charges from two columns 511 and 512 to one shared output circuit. Y-shaped buried diffusion 502 comprises a continuous n-doped region formed in a semiconductor substrate 501 and includes parallel upstream (first and second) elongated portions 502-1 and 502-2 that are connected to a downstream (third) elongated portion 502-3 by way of a V-shaped merge section 502-4. The continuous n-doped region is formed using known techniques such that image charges (comprising electrons) accumulated by pixels 520-1 and 520-2 are constrained to travel along upstream elongated portions 502-1 and 502-2, and are respectively directed by V-shaped merge section 502-4 into downstream elongated portion 502-3.

Pixels 520-1 and 520-2 are formed in respective associated columns 511 and 512 by way of polycrystalline silicon pixel gate structures 515-1, 515-2 and 515-3 respectively formed over upstream elongated portions 502-1 and 502-2. Additional pixels may be formed in each column 511 and 512 (e.g., above pixels 520-1 and 520-2 in the figure). Image charges generated by pixels 520-1 and 520-2 are constrained to move down columns 511 and 512 (i.e., by upstream elongated diffusion portions 502-1 and 502-2) three-phase pixel control signals PV1, PV2 and PV3 that are generated in the manner described below.

Similar to the previous embodiment, sensor 500 includes two rows of transfer gates 523-1 to 523-4, including first row (first and second) transfer gates 523-1 and 523-2 and second row (third and fourth) transfer gates 523-3 and 523-4. First row transfer gates 523-1 and 523-2 are formed by polycrystalline silicon transfer gate structures 504-11 and 504-12 respectively operably disposed over upstream (first and second) elongated diffusion portions 502-1 and 502-2 between pixels 520-1 and 520-2 and the second row transfer gates. Second row transfer gates 523-3 and 523-4 are formed by polycrystalline silicon transfer gate structures 504-21 and 504-22 respectively operably disposed over elongated diffusion portions 502-1 and 502-2 between the first row transfer gates and V-shaped merge section 502-4. With this arrangement, (first and third) transfer gates 523-1 and 523-3 are configured to transfer image charges passed along channel 511 toward V-shaped merge section 502-4, and (second and fourth) transfer gates 523-2 and 523-4 are configured to transfer image charges passed along associated second channel 512 toward V-shaped merge section 502-4.

As set forth above, the transfer gate structures forming transfer gates 523-1 to 523-4 are effectively cross-coupled to facilitate efficient and reliable transfer of image charges from columns 511 and 512 to summing gate 524. Specifically, (first) transfer gate 523-1 and (fourth) transfer gate 523-4 are coupled to receive transfer gate control signal C1, which is transmitted on signal line 562-1, and (second) transfer gate 523-2 and (third) transfer gate 523-3 are coupled to receive transfer gate control signal C2, which is transmitted on signal line 562-2. This arrangement is referred to herein as effective cross-coupling because first and fourth transfer gates 523-1 and 523-4 are effectively coupled such that when (first) transfer gate control signal C1 is applied on first transfer gate structure 504-11, it is substantially simultaneously applied to (fourth) transfer gate structure 504-22, and second and third transfer gates 523-2 and 523-3 are effectively coupled such that when (second) transfer gate control signal C2 is applied to second transfer gate structure 504-12, it is substantially simultaneously applied to third transfer gate structure 504-21.

According to the depicted embodiment, the effective cross-coupling is at least partially achieved using one or more conductive (e.g., metal or doped polycrystalline silicon) linking structures that are connected between the two associated transfer gate structures. Referring to the region between the two columns in FIG. 5, first-row, first column transfer gate structure 504-11 is implemented as a horizontally oriented elongated polycrystalline silicon gate structure that extends to the right over the region separating columns 511 and 512, and second-row, second column transfer gate structure 504-22 is implemented as a horizontally oriented elongated polycrystalline silicon gate structure that extends to the left over the region separating columns 511 and 512. By overlapping the portions of transfer gate structures 504-11 and 504-22 in the horizontal direction, these two structures are electrically connected by way of conductive linking structure 532, which extends parallel to the column (vertical) direction. This linking arrangement facilitates reliable cross-couple control over associated transfer gate structures 504-11 and 504-22 in that, when transfer gate control signal C1 is applied to transfer gate structure 504-11, it is also substantially simultaneously applied to transfer gate structure 504-22 (i.e., by way of transmission over conductive linking structure 532).

A summing gate 524 is formed over V-shaped merge region 502-4 such that summing gate 524 functions to transfer image charges from either column 511 or 512 to downstream elongated diffusion portion 502-3. In one embodiment, summing gate 524 is implemented as a tapered polycrystalline silicon structure having an upstream edge 505A having a width W1 (i.e., measured in a direction perpendicular to columns 511 and 512) that is longer than a width W2 of its downstream edge 505A. This tapered summing gate structure facilitates efficient transfer of image charges from upstream elongated diffusion portions 502-1 and 502-2 to downstream elongated diffusion portion 502-3. Summing gate 505 is controlled by summing gate control signal SG to function in a manner similar to that described above with reference to summing gate 404-4, where a clock rate of summing gate control signal SG is two times faster than a line clock rate of the pixel control signals PV1, PV2 and PV3. In one embodiment, an additional tapered output gate structure (see structure 506, FIG. 5C) is disposed over a downstream portion of the V-shaped merge section 502-4 (i.e., between summing gate structure 505 and downstream elongated diffusion portion 502-3), and functions to prevent charge spill from the sense node back to summing gate 505.

During operation, image charges are generated in pixels 520-1 and 520-2 are transferred along columns 511 and 512 at a clock rate determined by line clock signals PV1, PV2 and PV3. Examples of waveforms of the various control signals are shown in FIGS. 8A, 8B and 8C. A simplified explanation follows of how waveforms such as those shown in FIGS. 8A, 8B and 8C can transfer charges in sensor 500. Note that FIGS. 8A, 8B and 8C include the control signal VB for a buffer gate which is present in some embodiments, but not depicted in FIG. 5. When transfer gate control signal C1 generates a high voltage (i.e. a voltage that is more positive than a low voltage) on signal line 562-1, potential wells are formed under transfer gate structures 504-11 and 504-22. Similarly when transfer gate control signal C2 generates a high voltage on signal line 562-2, potential wells are formed under transfer gate structures 504-12 and 504-21. When line clock signal PV3 is driven to a low voltage, image charges transfer from under pixels 520-1 and 520-2 (or, alternatively, when the control signal VB on the buffer gate in, for example, FIGS. 5G and 8A is driven to a low voltage, image charges transfer from under intervening buffer gates in columns 511 and 512, not shown) to under transfer gate structures 504-11 and 504-12. Implanted barriers at appropriate locations in channels 502-1 and 502-2 prevent the charges from transferring under gates 504-21 and 504-22 while control signals C1 and C2 are at approximately equal potentials. The use of implanted barriers to enable two-phase clocking in CCDs is well known. Next, transfer gate control signal C1 toggles such that the voltage on signal line 562-1 switches from high to low, while transfer gate control signal C2 is still high, whereby potential wells under transfer gates 504-11 and 504-22 collapse. Thus, the image charge under transfer gate 504-11 moves under transfer gate 504-21, and an image charge under transfer gate 504-22 moves under summing gate 505. When transfer gate control signal C2 switches from high to low, the image charge under transfer gate 504-21 moves under summing gate structure 505 while the image charge under transfer gate 504-12 moves under transfer gate 504-22. By way of example but not as a limitation, a high voltage may mean a voltage of approximately +5V, whereas a low voltage may mean a voltage of approximately −5V, relative to the potential of the substrate. One skilled in the relevant art understands that the appropriate voltages to use depend on many factors including doping level(s) in the buried channel, doping levels of the polysilicon gate electrodes, thicknesses and dielectric constants of dielectric layers, and dimensions and full-well capacity of the pixels and gate structures.

By repeating the operations described above, image charges generated by pixels in two columns (i.e., columns 511 and 512) are sequentially transferred to a single output circuit by way of shared (common) summing gate 505. Simultaneously, other pairs of columns sequentially clock their charges under the corresponding common summing gates provided for those pairs of columns. Exemplary voltage waveforms and timing configurations of the above clock signals are depicted in additional detail in FIGS. 8A, 8B, and 8C. In the preferred embodiment shown in FIG. 5, each column utilizes one transfer gate pair to clock image charge to the common summing gate. In other embodiments, two or more transfer gate pairs per column could be used to implement other charge transfer schemes. Note that sensor 500 may also be operated to sum charges from the two columns in summing gate 505 by reading out summing gate 505 at the same rate as the line clock instead of at twice the line clock frequency. This allows an instrument incorporating sensor 500 to have different operating modes that trade off spatial resolution for improved signal-to-noise ratio.

Referring to the lower portion of FIG. 5, the output circuit is implemented by a floating diffusion 507 formed in downstream elongated diffusion portion 502-3, and an on-chip pre-amplifier circuit 509 that is operably coupled to floating diffusion 507 by way of a suitable (metal or polysilicon) conductive structure 535. On-chip pre-amplifier 509 functions to convert image charges stored on floating diffusion 507 to voltage signals, and to deliver buffered voltage signals $V_{OUT}$ to output terminal 510. A pre-amplifier is widely used in CCD sensors to amplify and/or buffer the signal and prepare it for further processing. Multiple pre-amplifier and buffer configurations known in the art are suitable for use in dual-column-parallel CCD image sensor 500. Pre-amplifier 509 may comprise multiple transistors, resistors, and capacitors. By way of example, amplifier 509 may comprise two stages of source followers. The first stage source follower includes a gain transistor M1 and a current sink transistor M2; the second stage source follower includes a gain transistor M3, whereby output terminal 510 of amplifier 509 is formed by the source terminal of transistor M3. A reset transistor 508 is provided that includes a source terminal connected to floating diffusion 507, a gate terminal controlled by a reset clock signal RG, and a drain terminal connected to a reset voltage RD. A typical operation (integration and readout) cycle begins by resetting floating diffusion 507 to voltage RD by way of toggling reset transistor 508, waiting a predetermined integration period, then sampling output voltage at output terminal 510. During the integration period, the voltage level at output terminal 510 changes (becomes more negative) by an amount proportional to the image charge funneled to floating diffusion 507. During the readout period, an ADC (not shown) measures the analog voltage level and converts it to a digital number for further signal processing. The ADC may be located on chip or off chip.

FIGS. 5A to 5G illustrate key fabrication features associated with the production of sensor 500, and include additional features not illustrated in FIG. 5. For example, FIGS. 5A to 5G show five columns instead of only two, and also show optional elements such as buffer gates. Note that only a portion of the pre-amplifiers is shown for brevity, and that additional features of the pre-amplifiers are described below with reference to FIG. 7.

Figure 5A:
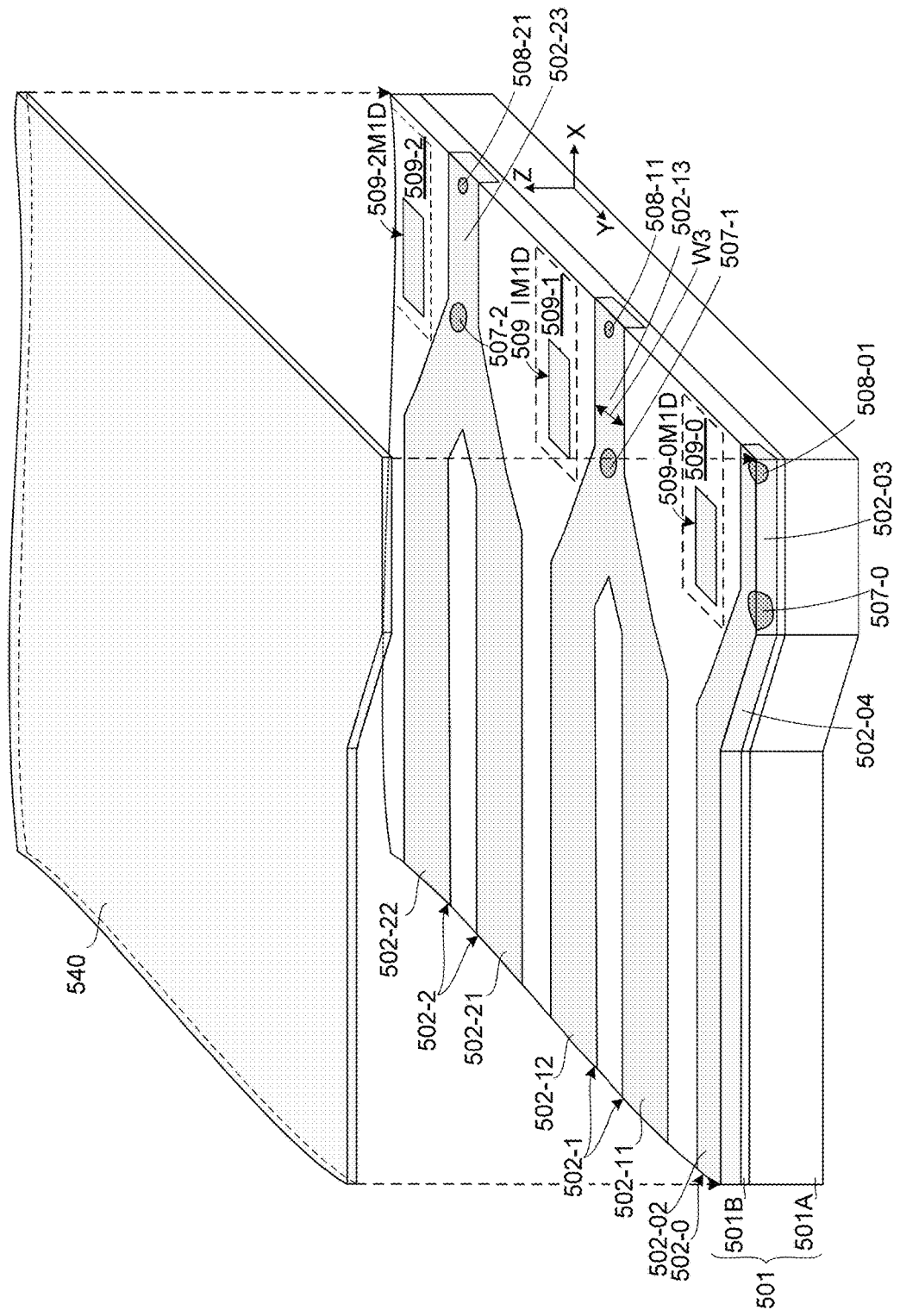
FIGS. 5A, 5B, 5C, 5D, 5E, 5F and 5G are partial exploded perspective views illustrating the fabrication of the exemplary dual-column-parallel CCD sensor of FIG. 5.

FIG. 5A shows substrate 501 after the diffusion of suitable dopants using known (e.g., CMOS) semiconductor processing techniques, and prior to the formation of a lowermost dielectric layer 540 over the substrate's upper surface. As described above, sensor 500 includes three Y-shaped buried diffusions (channels) 502-0, 502-1 and 502-2, with only a portion of diffusion 502-0 shown for illustrative purposes. Each Y-shaped buried diffusion includes upstream elongated portions that form five channels: upstream elongated diffusion portions 502-11 and 502-12 of diffusion 502-1 form first and second channels, upper elongated diffusion portions 502-21 and 502-22 of diffusion 502-2 form third and fourth channels, and upstream elongated diffusion portion 502-01 of diffusion 502-0 forms the fifth channel. In one embodiment, buried channel diffusions 502-0, 502-1 and 502-2 are formed by an n-type dopant diffused into an epitaxial silicon layer 501B formed on a p-type monocrystalline silicon substrate 501A using known techniques. In an alternative embodiment, the buried channels could be formed by p-type doping over an n-type semiconductor substrate in which an image charge (comprising holes) accumulates and transfers. The width of the V-shaped buried channel portions gradually tapers to downstream buried diffusion portions 502-03, 502-13 and 502-23. The minimum width of the downstream buried diffusion portions (e.g., width W3 of buried portion 502-13) is set such that the subsequently formed summing gates are capable of accommodating image charges passed from both of the two associated upstream buried diffusion portions (e.g., buried portions 502-11 and 502-12).

Floating diffusions 507-0, 507-1 and 507-2 and reset diffusions 508-01, 508-11 and 508-21 are formed by an n+ dopant diffused into the narrow ends of buried channels 502-0, 502-1 and 502-2, respectively. Preferably floating diffusion 507 is formed with a minimum possible size consistent with the full-well signal level so as to reduce the capacitance of the floating diffusion. A reduction in floating diffusion capacitance leads to an increase in charge conversion efficiency (CCE) and thereby an improved signal-to-noise ratio at output terminal 510.

Also shown in FIG. 5A are diffusions 509-0M1D, 509-1M1D, 509-2M1D, which form source, drain and channel regions of first-stage transistors of pre-amplifiers 509-0, 509-1 and 509-2. The relevance of these diffusions is discussed below with reference to the formation of polycrystalline silicon structures that connect to floating diffusions 509-0, 509-1 and 509-2.

Figure 5B:
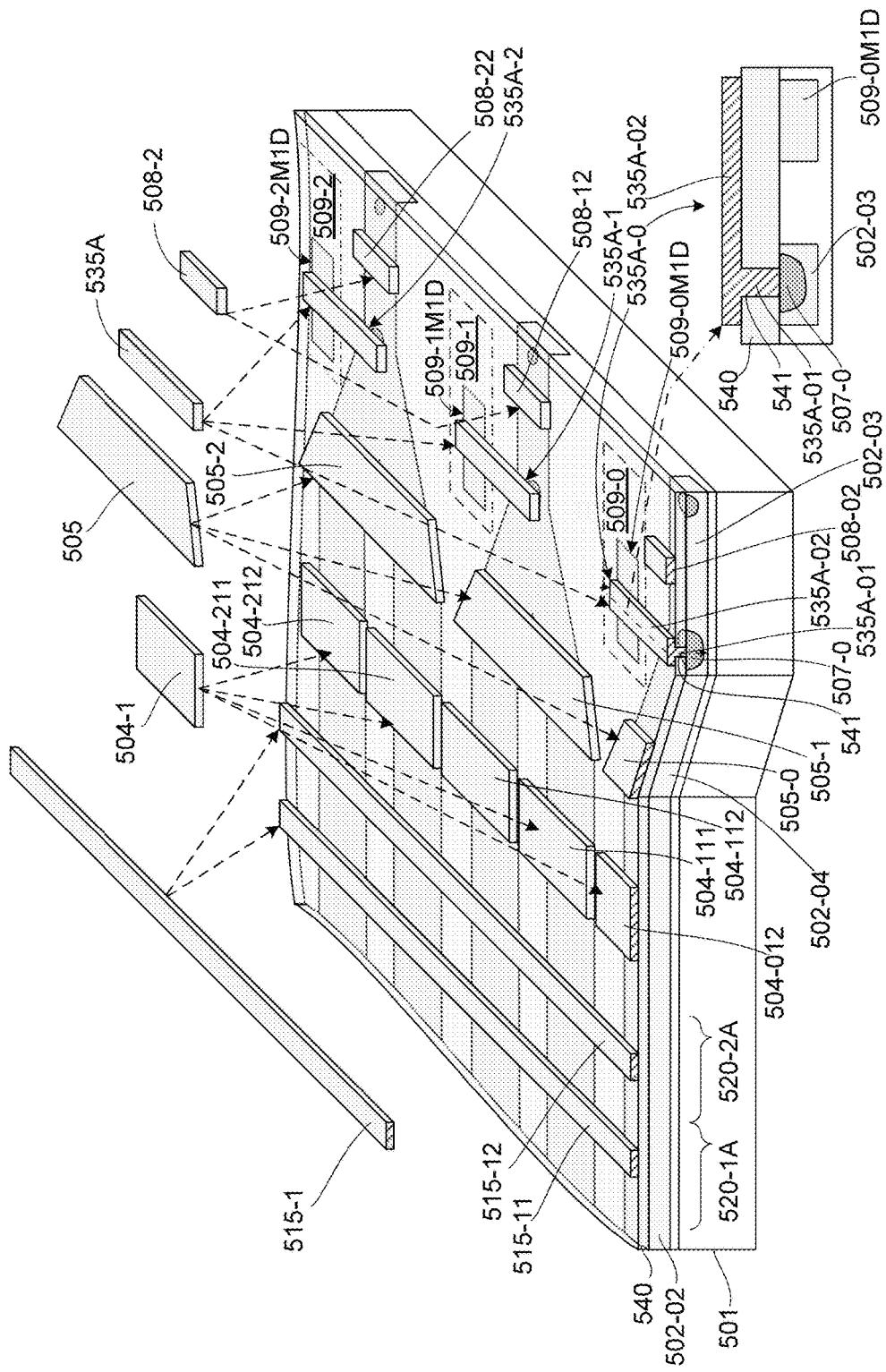

FIG. 5B depicts a first polycrystalline silicon process during which a first set of polycrystalline silicon structures (known as "first poly structures") are formed on dielectric layer 540. These first poly structures include first pixel gate structures 515-1, first row transfer gate structures 504-1, summing gate structures 505, interconnect structures 535A, and reset gate structures 508-2. Referring to the left side of FIG. 5B, the depicted first poly structures include two pixel gate structures 515-11 and 515-12, which correspond with two rows of pixels 520-1A and 520-1B. Five first-row transfer gate structures 504-02, 504-11, 504-12, 504-21 and 504-22 are formed as separate structures disposed over corresponding upstream elongated diffusion portions (e.g., first-row transfer gate structure 504-02 extends over upstream elongated diffusion portion 502-02). Three summing gate structures 505-0, 505-1 and 505-2 are formed over respective V-shaped diffusion portions (e.g., summing gate structure 505-0 is disposed over V-shaped diffusion portion 502-04). Three conductive structures 535A-0, 535A-1 and 535A-2 are formed over respective floating diffusions (e.g., conductive structure 535A-0 is disposed over floating diffusion 507-0). Finally, three reset gate structures 508-01, 508-11 and 508-21 are formed over respective downstream diffusion portions (e.g., reset gate structure 508-01 is disposed over downstream diffusion portion 502-03).

As indicated by the partial cross-section located in the lower right portion of FIG. 5B, in one embodiment each conductive structures 535A-0, 535A-1 and 535A-2 are formed such that they include lower/vertical poly portions that extend through dielectric layer 540 to corresponding floating diffusions, and upper/horizontal poly portions that extend horizontally to form first-stage gain transistor gate structures. For example, referring to the cross section, poly portion 535A-0 includes lower/vertical poly portion 535A-01 that extends through associated contact hole 541 formed in dielectric layer 540 and contacts floating diffusion 507-0, and upper/horizontal poly portion 535A-02 that extend horizontally from an upper end of lower/vertical poly portion 535A-01 across the upper surface of dielectric layer 540, and extends over diffusions 509-0M1D to provide a gate structure for the first-stage transistors of pre-amplifier 509-0. This arrangement facilitates operable connection between each sense node and the associated pre-amplifier without the need for a metal interconnect, thereby reducing floating diffusion capacitance and increasing charge conversion efficiency, thus improving the sensor's signal-to-noise ratio. Moreover, in one embodiment the floating diffusions are self-aligned to conductive structures 535A-0, 535A-1 and 535A-2 by way of forming the floating diffusions through the same opening as that used to form the connecting poly portions. In a conventional CCD sensor, a floating diffusion is formed prior to contact hole etching and polysilicon (i.e. polycrystalline silicon) deposition, and any misalignment between the floating diffusion, contact hole, and polysilicon introduces parasitic capacitance. In the preferred embodiment, contact holes 541 are first etched through dielectric layer 540, followed by doping of floating diffusion 507-0, and then deposition of the first polysilicon material, whereby conductive structure 535A-0 is self-aligned to floating diffusion 507-0. Thus self-aligned floating diffusions are formed and directly connected to the polysilicon gates of first-stage transistors M1 without metal interconnect. This technique can further reduce the floating diffusion capacitance, increase charge conversion efficiency, and thereby improve the signal-to-noise ratio in the CCD sensors described herein. U.S. Pat. No. 3,699,646, entitled "Integrated circuit structure and method for making integrated circuit structure", issued on Oct. 24, 1972, to Vadasz and incorporated herein by reference, describes additional aspects and details of a buried contact and self-aligned diffusion.

Floating diffusion 507-0 is a heavily doped region that is described in detail in FIG. 5 and its associated description. A reset transistor MR is adjacent to the other side of the floating diffusion, which also functions as the source terminal of the reset transistor. After resetting the floating diffusion to a reset voltage RD by way of toggling reset transistor MR, image charge is transferred by output gate OG to the floating diffusion and read out by the on-chip amplifier.

Figure 5C:
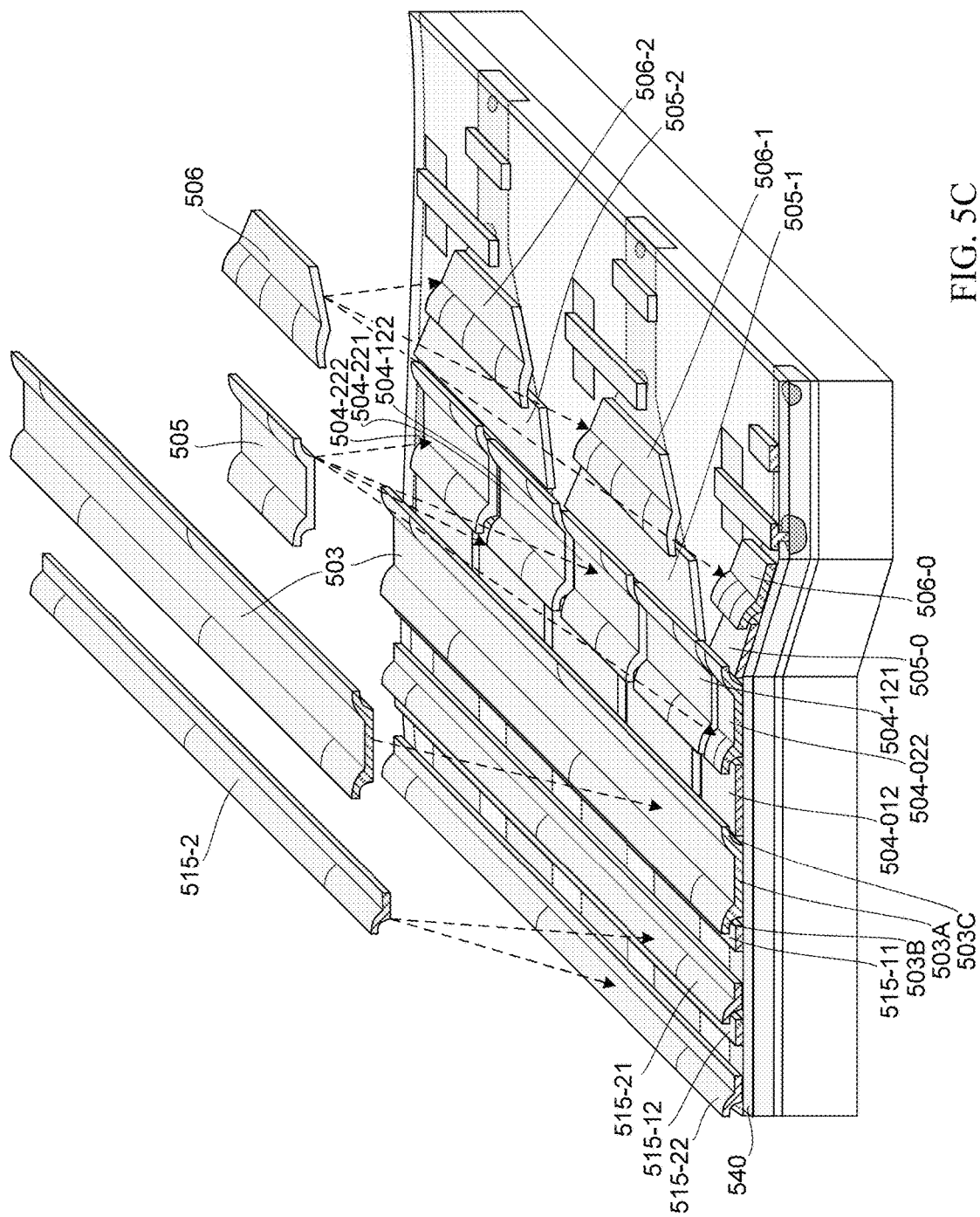

FIG. 5C depicts a second polycrystalline silicon process during which second poly structures are formed on dielectric layer 540. The second poly structures include second pixel gate structures 515-2, second row transfer gate structures 504-2, and output gate structures 506. Second pixel gate structures 515-2 include pixel gate structures 515-21 and 515-22 that are partially formed on the upper surface of dielectric layer 540, and include raised portions that extend over adjacent first poly structures (e.g., second poly gate structure 515-21 partially overlaps first pixel gate structure 515-12). Similarly, buffer gate structure 503 includes a flat central portion 503A that is partially formed on the upper surface of dielectric layer 540, a raised first edge portion 503B formed such that it extends over one edge of first pixel gate structure 515-11, and a raised second edge portion 503C such that it extends over first (left side) edges of the first-row transfer gate structures (e.g., over transfer gate structure 504-012). Buffer gate 503 functions to momentarily store image charges moving out of the pixel columns, and to transfer the image charges to the transfer gates. Although one buffer gate 503 is shown for each column, none, two or more buffer gates could be used. In one preferred embodiment, an even number of rows, such as two rows, of buffer gates are used, so that the clock signals that drive the odd rows are substantially 180° out of phase with the clocks that drive the even rows and so create minimal substrate currents and add little noise to the output. Five separate second-row transfer gate structures 504-022, 504-121, 504-122, 504-221, 504-222 are formed in a manner similar to buffer gate structure 503 such that each includes a flat central portion, a raised first edge portion that extends over second (right side) edges of the first-row transfer gate structures, and a raised second edge that extend over the left-side edges of summing gate structures 505. For example, second-row transfer gate structure 504-022 includes a raised first edge portion that extends over right the side edge of first-row transfer gate structure 504-012, and a raised second edge that extends over a first (left side edge) of summing gate structures 505-0. Three output gate structures 506-0, 506-1 and 506-2 are formed in a similar manner such that each includes a flat portion and one raised edge portion that extends over second (right side) edges of summing gate structures 505-0, 506-1 and 506-2, respectively. The depicted overlaps of second poly structures over first poly structures are achieved using known techniques, and serve to prevent incomplete transfer of image charges by reducing potential barriers in the buried diffusion channels between gates. Other known techniques may also be used, such as vertically arranging the gate structures disposed on different dielectric gate insulators. Depending on the sensor applications and charge transfer requirements, each of the above gates could be implemented by one or more polycrystalline or amorphous silicon gate structures.

Implanted barriers of appropriate heights are placed at appropriate locations in the buried channel under the buffer and transfer gates such that a lower buried-channel potential is achieved near one side of each gate than the other side. When one gate is at a high potential and an adjacent gate is at a low potential, this lower buried-channel potential creates a staircase-like potential that ensures that image charge only transfers in the desired direction. When two adjacent gates are at equal potentials, this lower buried-channel potential creates a barrier that prevents charges from drifting from one gate to the other.

Output gate structures 506-0, 506-1 and 506-2 are disposed over downstream portions of the V-shaped merge sections of Y-shaped buried diffusions 502-0, 502-1 and 502-2, respectively (i.e., between the summing gate structures and the downstream elongated diffusion portions), and function to prevent charge spill from the sense nodes back to summing gates 505-0, 505-1 and 505-2. Each output gate 506-0 to 506-2 includes a polycrystalline (or amorphous) silicon gate structure disposed on dielectric (gate insulator) layer 140, and is biased by such a voltage that an appropriate electric potential is achieved under the output gate. During charge transfer from associated summing gates 505-0 to 505-2 to floating diffusions 507-0 to 507-2, the potential under output gate structures 506-0 to 506-2 is higher than that under the common summing gate region and lower than that under the floating diffusion region; image charge moves up the electric potential "staircase" and smoothly transfers from the summing gates to the floating diffusions. After a packet of image charge is transferred, the voltage on summing gates 505-0 to 505-2 switches from low to high, the potential under each summing gate becomes higher than that under the adjacent output gate; image charge cannot spill back to the summing gate due to the potential barrier under the output gate. In a manner similar to summing gates 505-0 to 505-2, output gate structures 506-0 to 506-2 are laid out with widths gradually tapering towards floating diffusions 507-0 to 507-2, respectively.

Figure 5D:
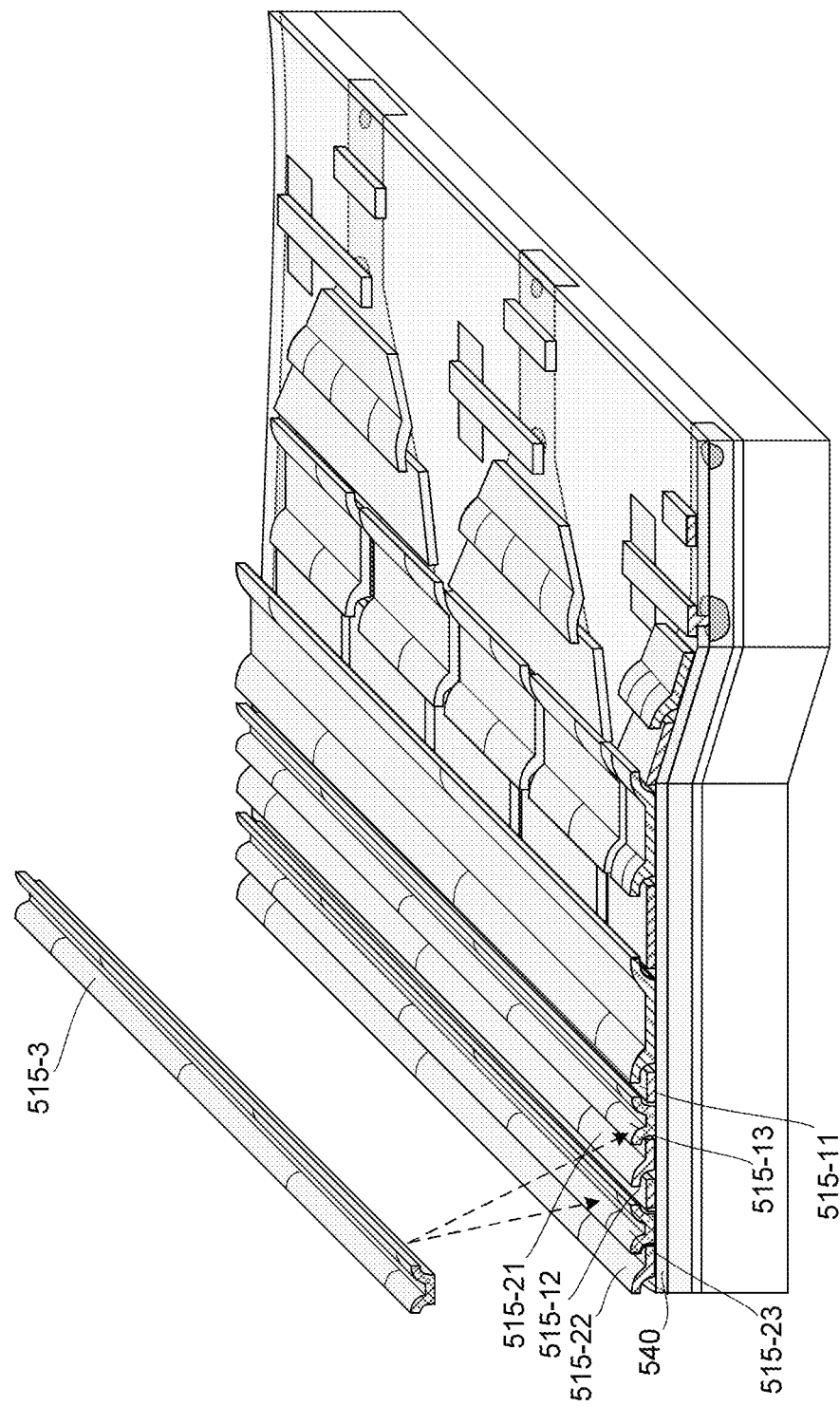

FIG. 5D depicts a third polycrystalline silicon process during which third poly structures are formed on dielectric layer 540. The third poly process is typically used to form third pixel gate structures 515-3, which in the present example includes pixel gate structures 515-13 and 515-23 that are partially formed on the upper surface of dielectric layer 540, and include raised portions that extend over adjacent first poly and second poly structures. For example, third poly gate structure 515-13 partially overlaps the left-side edge of first pixel gate structure 515-11, and also partially overlaps a portion of second pixel gate structure 515-12. Similarly, third poly gate structure 515-23 partially overlaps the left-side edge of first pixel gate structure 515-21, and also partially overlaps a portion of second pixel gate structure 515-22. These third poly structures are also formed using known techniques.

A typical CCD manufacturing process uses three different polycrystalline silicon depositions to form the three pixel gate structures needed for the three-phase line (vertical) clock. The first, second and third polycrystalline structures depicted in FIGS. 5A-5D illustrate one way to fabricate sensor 500. Alternative combinations of first, second and third polycrystalline structures may be used to fabricate the sensor. For example, buffer, transfer, summing and output gates could be fabricated from second and third polycrystalline structures rather than from first and second polycrystalline structures. In another example, individual gates could be fabricated from a combination of two different polycrystalline layers.

Figure 5E:
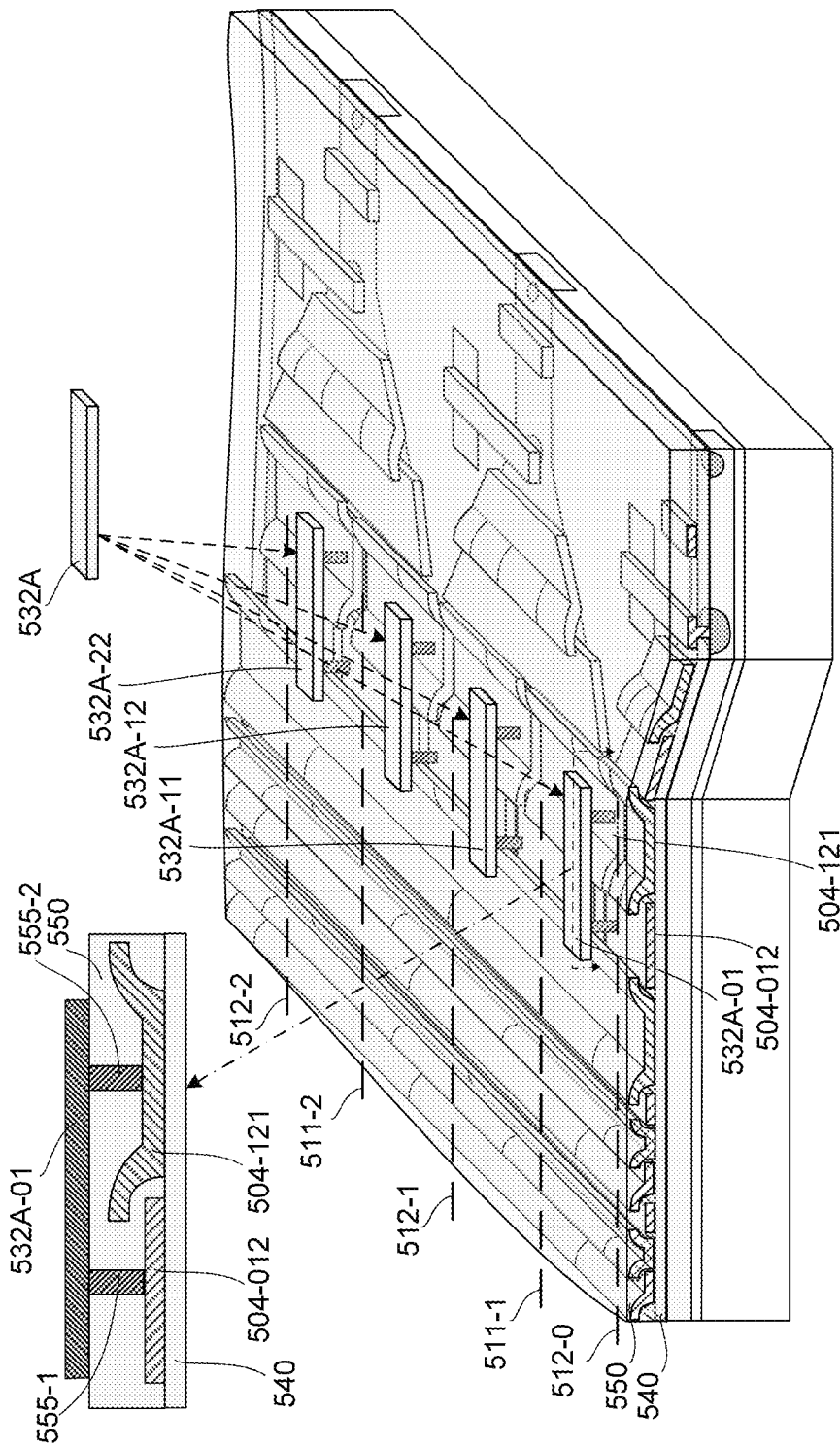

FIG. 5E depicts a first metallization (first metal) process during which a first layer of metal interconnect structures are formed over the poly structures. A pre-metal dielectric layer 550 is formed over the lower dielectric layer 540 and, optionally, planarized according to known techniques. Contact openings (vias) to underlying structures are then formed through the upper surface of the pre-metal dielectric layer 550, metal via structures are then formed in the via openings, and then a metal layer is deposited and patterned to form the first metal structures.

In accordance with the exemplary embodiment, the first metal process is utilized to form metal conductive linking structures 532A such that each first-row transfer gate structure is electrically connected to an associated second row transfer gate structure in a manner that satisfies the simultaneous gate control technique described above. Specifically, each first-row transfer gate structure in one column is connected to a second-row transfer gate structure in an adjacent column by way of an associated metal conductive linking structure 532A and corresponding metal vias. For example, first-row transfer gate structure 504-012 in column 512-0 is connected to second-row transfer gate structure 504-121 in adjacent column 511-1 by way of metal conductive linking structure 532A-01, and as indicated by the partial cross-section provided in the upper left portion of FIG. 5E, the connection is facilitated by metal vias 555-1 and 555-2 that pass through pre-metal dielectric layer 550. Similarly, the first-row transfer gate structures disposed in columns 511-1, 512-1 and 511-2 are connected to second-row transfer gate structures in columns 512-1, 511-2 and 512-2, respectively, by way of metal conductive linking structures 532A-11, 532A-12 and 532A-22, respectively.

Figure 5F:
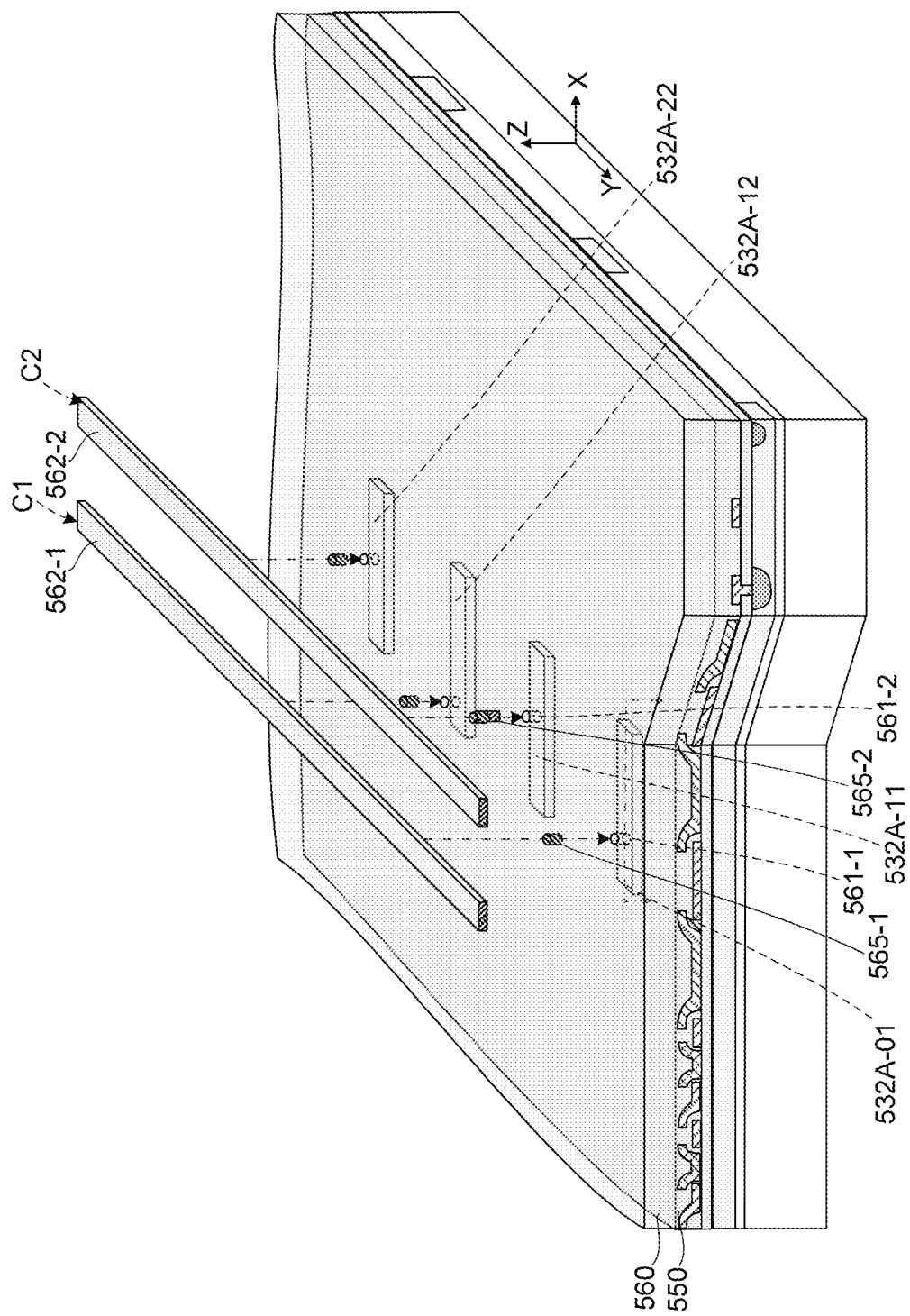
Figure 5G:
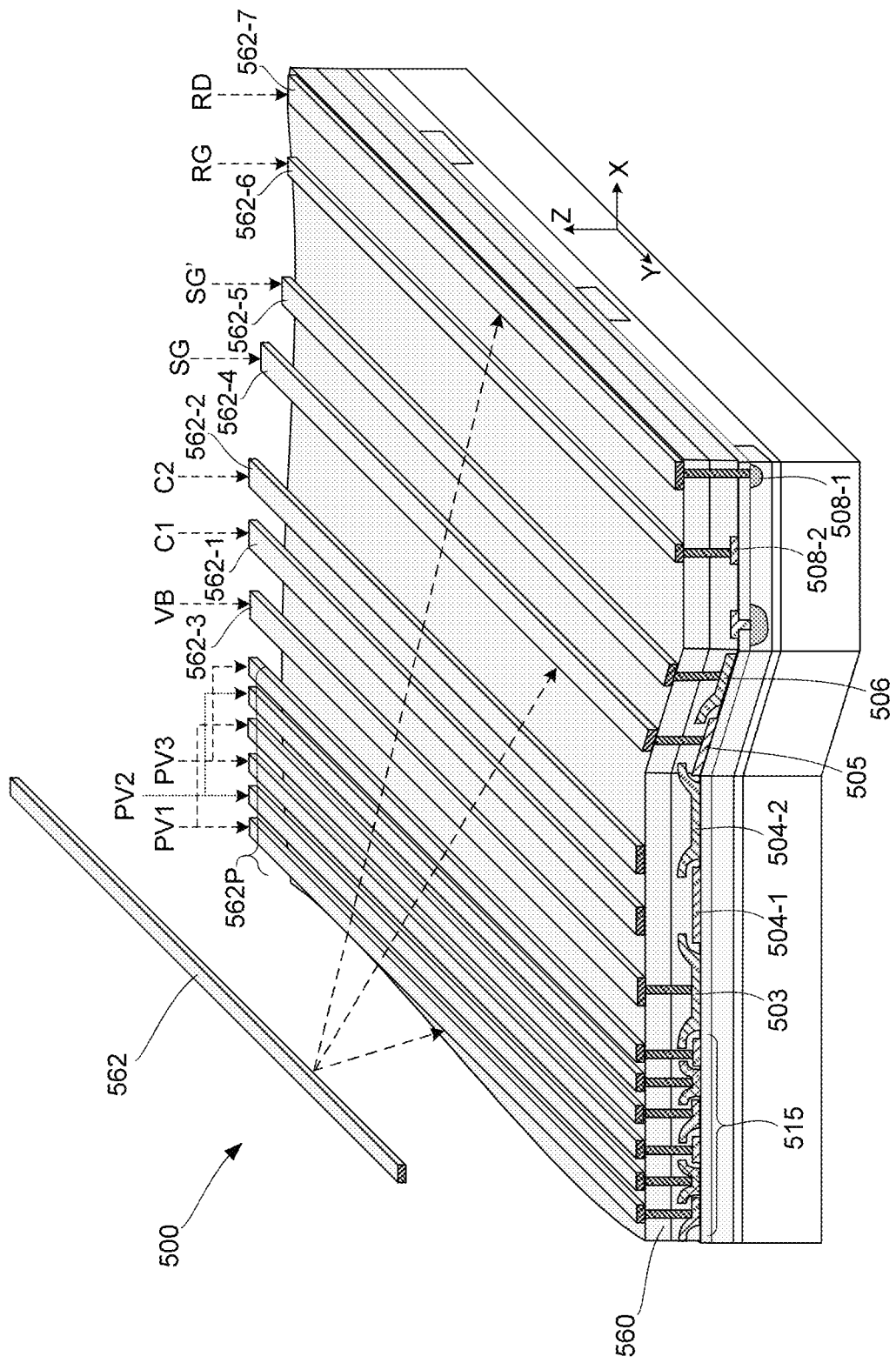

FIGS. 5F and 5G depict a second metallization (second metal) process during which a second layer of metal interconnect structures are formed over the poly structures and first metal structures. The second metal process begins by depositing and, optionally, planarizing an inter-metal dielectric material over pre-metal dielectric layer 550 and the first metal structures to form an inter-metal dielectric layer 560. Contact openings (vias) to underlying structures are then formed through the upper surface of the inter-metal dielectric layer 560, metal via structures are then formed in the via openings, and then a second metal layer is deposited and patterned to form the second metal structures. In the exemplary embodiment, the second metal process is utilized to form metal signal lines utilized to conduct to the various poly gate structures appropriate bias voltages and clock/ control signals, which are generated by an external control circuit (not shown) and applied onto the second metal signal lines by way of solder bumps or wire bonds according to known techniques. For clarity, FIG. 5F shows only the second metal (signal line) structures 562-1 and 562-2 that are used to transmit transfer gate control signals C1 and C2 to metal conductive linking structures 532A-01, 532A-11, 532A-12 and 532A-22, and the remaining second metal structures formed during the second metal process are depicted in FIG. 5G; it is understood that all of these second metal structures are formed concurrently.

Referring to FIG. 5F, to facilitate the transfer gate functionality described above, second metal (signal line) structures 562-1 and 562-2 are connected to metal conductive linking structures 532A-01, 532A-11, 532A-12 and 532A-22 in an alternating arrangement. That is, signal line structure 562-1 is connected to conductive linking structures 532A-01 by way of a metal via structure 565-1 that extends through a via opening 561-1 defined in (i.e., etched into) inter-metal dielectric layer 560. According to the alternating arrangement, signal line structure 562-2 is connected to next-in-line conductive linking structures 532A-11 by way of a metal via structure 565-2 that extends through a via opening 561-2 defined in inter-metal dielectric layer 560, signal line structure 562-1 is connected to next-in-line conductive linking structures 532A-12, and signal line structure 562-1 is connected to next-in-line conductive linking structures 532A-12. Note that signal lines 562-1 and 562-2 extend perpendicular to (i.e., in the Y-axis direction) metal conductive linking structures 532A-01, 532A-11, 532A-12 and 532A-22, which in the exemplary embodiment extend in the X-axis direction.

FIG. 5G shows the remaining second metal (signal line) structures 562 and exemplary via contact structures that are formed on inter-metal dielectric 560 and utilized to transmit control and bias signals to corresponding gate structures and diffusions of sensor 500. Specifically, six pixel signal lines 562P are utilized to transmit line clock signals P1V, P2V and P3V to pixel gate structures 515, a buffer signal line 562-3 is utilized to transmit a buffer control (clock) signal VB to buffer gate structure 503, signal lines 562-4 and 562-5 are utilized to transmit summing gate control signal SG to summing gate structure 505 and output gate 506, a reset gate signal line 562-3 is utilized to transmit a reset gate control signal RG to reset gate structures 508-2, and a reset bias signal line 562-3 is utilized to transmit a reset bias signal RD to reset diffusions 508-1. Note that pixel signal lines 562P are indicated as straight metal lines for simplicity, but in practice these lines are often arranged in a V-shaped pattern in order to meet minimum feature (e.g., line width and spacing) requirements of the semiconductor process utilized to fabricate sensor 500. Note also that connections between transfer gate signal lines 562-1 and 562-2 and associated transfer gate structures 504-1 and 504-2 are shown and described above with reference to FIG. 5F.

Figure 6:
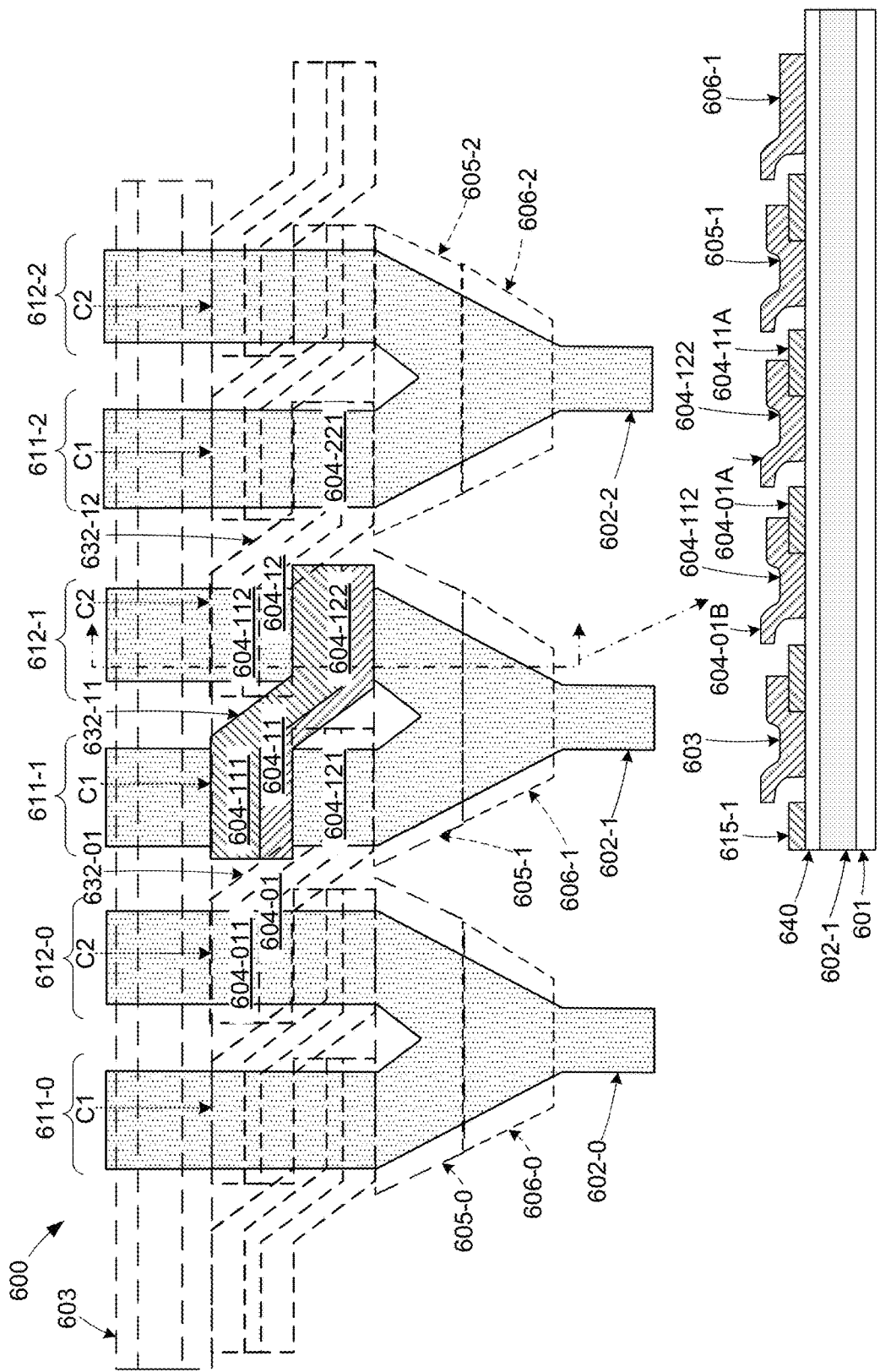
FIG. 6 is a simplified plan view showing an exemplary layout for a self-aligned floating diffusion with a polysilicon transfer gate structure in accordance with one embodiment of the present invention.

FIG. 6 illustrates a partial dual-column-parallel CCD image sensor 600 according to another exemplary preferred embodiment of the present invention. Similar to sensor 500 (described above), sensor 600 utilizes Y-shaped buried diffusions 602-0, 602-1 and 602-2 to facilitate the transfer of image charges from pixels (not shown) disposed in associated columns 611-0 to 612-2, where each associated pair of columns (e.g., columns 611-1 and 611-2) share a single sense node formed in the manner described above. Similar to the previous embodiment, sensor 600 includes a row of buffer gates controlled by a polycrystalline silicon buffer gate structure 603, two rows of transfer gates formed by polycrystalline silicon transfer gate structures (described below), tapered polycrystalline silicon summing gate structures 605-0 to 605-2, and tapered polycrystalline silicon output gate structures 606-0 to 606-2. Image sensor 600 operates substantially as described above with reference to sensor 500.

Sensor 600 differs from sensor 500 in that the two rows of transfer gates utilized by sensor 600 are implemented using integral "Z" shaped composite polycrystalline silicon structures. As indicated in the center of FIG. 6, one such "Z" shaped composite polycrystalline silicon structure 604-11 includes a first horizontal portion that forms first-row (first) transfer gate structure 604-111, a second horizontal portion that forms second row (fourth) transfer gate structure 604-122, and a diagonal (first) polycrystalline silicon structure conductive linking structure 632-11 that integrally connects transfer gate structures 604-111 and 604-122. Additional "Z" shaped composite polycrystalline silicon structures (e.g., structures 604-01 and 604-12) are indicated in dashed lines in order to more clearly depict the features of transfer gate structure 604-111, but are understood to be essentially identical in structure. Similar to sensor 500, the "Z" shaped composite polycrystalline silicon structures provide effective cross-coupling between associated first- and second-row transfer gates by way of applying transfer control signals C1 and C2 to "Z" shaped composite polycrystalline silicon structures in an alternating pattern. Specifically, associated first row (first) transfer gate structure 604-111 and second-row (fourth) transfer gate 604-122 are coupled through the integral connection formed by polycrystalline silicon structure 604-11 such that a first control signal C1 applied to transfer gate structure 604-111 is transmitted by way of conductive linking structure 632-11 to transfer gate 604-122. Second-row transfer gate 604-121 is formed by the lower horizontal portion of "Z" shaped composite polycrystalline silicon structure 604-01, and associated first-row transfer gate 604-112 is formed by the upper horizontal portion of "Z" shaped composite polycrystalline silicon structure 604-12. Polycrystalline silicon structures 604-01 and 604-12 are disposed on opposite sides of polycrystalline silicon structure 604-11, and therefore are connected to receive control signal C2, thereby establishing an effective coupling between associated transfer gate structures 604-121 and 604-112 such that when control signal C2 applied to transfer gate structure 604-121 (e.g., by way of first row transfer gate structure 604-011 and conductive linking structure 632-01), it is also substantially simultaneously applied to associated first-row transfer gate structure 604-112 (which passes control signal to second-row transfer gate 604-221 by way of conductive linking structure 632-12).

The cross-section provided at the bottom of FIG. 6 indicates one possible approach for fabricating sensor 600. First poly structures are formed by way of depositing the first polycrystalline silicon layer, patterning the layer, etching the layer, and then oxidizing the remaining poly structures in the normal manner utilized in the fabrication of CCDs. In the cross-section, these first poly structures include pixel structure 615 and first poly portions of the composite polycrystalline silicon structures (e.g., portions 604-01A and 604-11A of "Z" shaped composite polycrystalline silicon structures 604-01 and 604-11, which form first-row transfer gate 604-112 and second row transfer gate 604-122. An additional mask is then used to expose the upper surfaces of first poly portions 604-01A and 604-11A, and a suitable etchant is used to remove the oxide in order to facilitate electrical connection from these first poly structures to the subsequently formed second poly structures. The second poly process is them performed during which second poly portions 604-01B and 604-11B are formed over the first poly portions to complete the composite polycrystalline silicon structures. To provide the preferred overlapping of adjacent structures, buffer gate structure 603 and summing gate structure 605-1 are also formed using similar composite polysilicon structures, and output gate structure 606-1 is formed only by a second poly structure.

Figure 7:
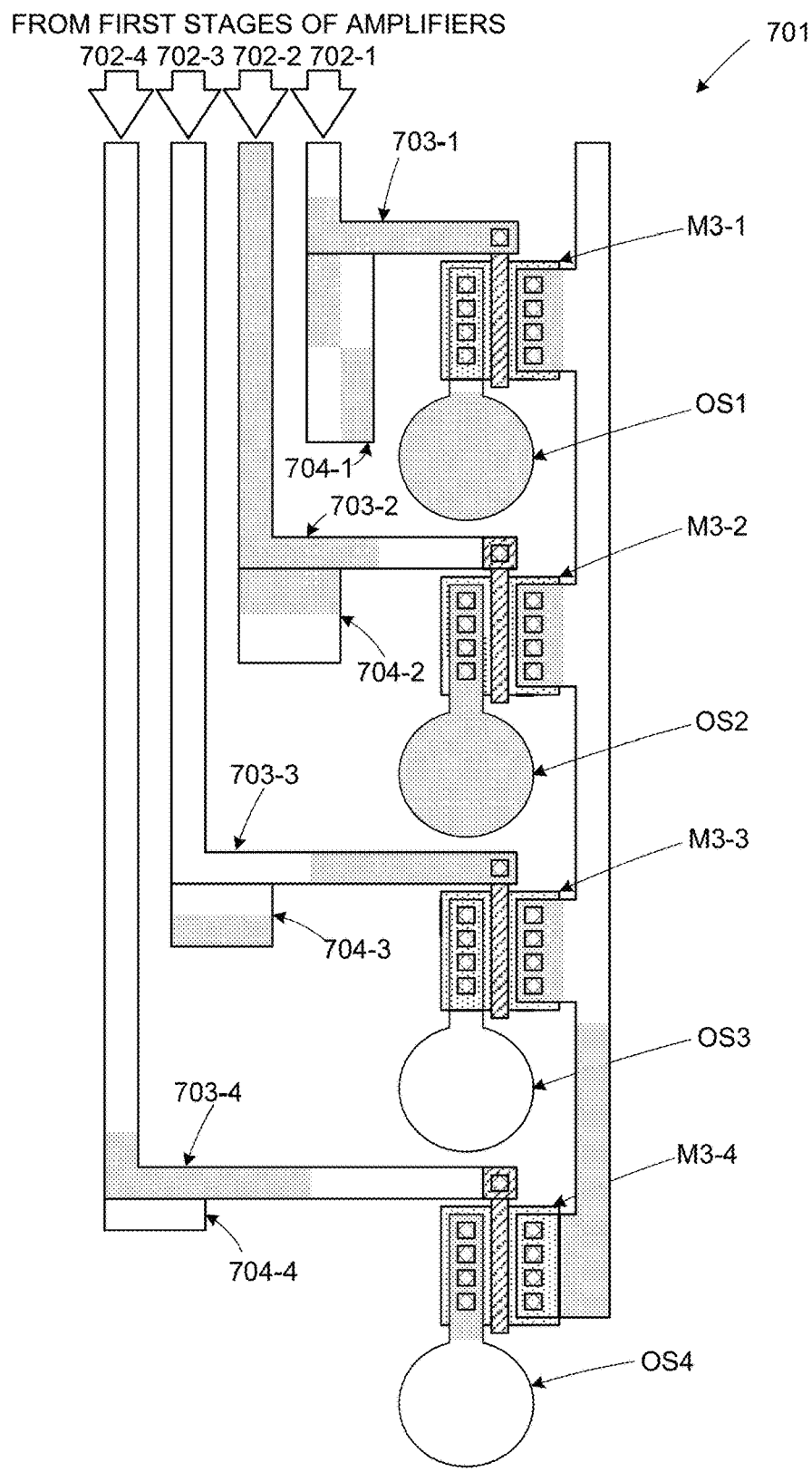
FIG. 7 is a simplified plan view showing an exemplary layout for metal interconnects of an on-chip amplifier in accordance with an alternative embodiment of the present invention.

FIG. 7 illustrates an exemplary layout for metal interconnects of an on-chip amplifier in which sensor outputs are optimized with equalized response and minimized crosstalk. Although various types of amplifiers could be used in CCD image sensors to convert image charge to voltage and drive external load at the output circuit of each channel, for illustrative purposes an amplifier comprising two stages of source followers is shown. In a preferred embodiment, one block of sensor outputs 701 comprises four channels of two-stage source follower amplifiers, whereby the first stage 702 is not shown in FIG. 7 for brevity (first stage 702 is located close to the floating diffusion as described above). Metal interconnects 703-1, 703-2, 703-3, and 703-4 connect the output terminals of the first stages 702-1, 702-2, 702-3, and 702-4 to the corresponding gate terminals of second stage transistors M3-1, M3-2, M3-3, and M3-4, respectively. The source terminals of the second stage transistors are connected to metal pads OS, namely, M3-1 to OS1, M3-2 to OS2, M3-3 to OS3, and M3-4 to OS4. In one embodiment, the CCD image sensor is flip-chip bonded to a second semiconductor (e.g., silicon) substrate with one or more ADCs and other signal processing circuits. An ADC reads a sensor output signal at a metal pad through a solder ball.

For each two-stage amplifier, the first stage transistors are kept small to minimize the load on the floating diffusion. This results in a low transconductance and low driving capability of first stage 702. For that reason, the second stage comprises a larger transistor M3 to drive an external circuit which may have an input capacitance as large as several pico-farads. As most heat dissipation happens in the second stage, it is important to spread out the large transistors M3-1, M3-2, M3-3, and M3-4. Furthermore in a preferred embodiment, metal pads OS1, OS2, OS3, and OS4 with a diameter of about 50 µm to 100 µm are used to provide good mechanical strength for flip-chip bonding. As the lateral width of a typical CCD pixel in a preferred embodiment is between about 10 µm and about 25 µm, four channels of sensor outputs can be grouped in block 701 in order to accommodate large transistors and metal pads. Depending on the pixel size, the output transistor size and the metal pad size, fewer or more channels could be grouped in one block of sensor outputs. However, the number of channels in one block should be as few as practical in order to keep the metal interconnects short enough for high bandwidth operation, while maintaining a high transistor and metal pad density. In preferred embodiments, the number of output channels in one block is between two and eight.

In one embodiment, transistors M3-1, M3-2, M3-3, and M3-4 are placed close to metal pads OS1, OS2, OS3, and OS4, respectively. Metal interconnects 703-1, 703-2, 703-3, and 703-4 between the first and second stages of the amplifiers have different lengths to spread out transistors M3-1, M3-2, M3-3, and M3-4 within the block. For the channel driving the metal pad OS1, which is closest to the first stage of the amplifier, metal interconnect 703-1 is the shortest and would add a minimal load to the first stage 702-1 in the absence of metal piece 704-1. For the channel driving the farthest metal pad OS4, metal interconnect 703-4 is the longest, and its capacitance becomes the dominant contributor to the total load on the first stage 702-4. Metal pieces 704-1, 704-2, 704-3, and 704-4 with successively smaller areas are added to metal interconnects 703-1, 703-2, 703-3, and 703-4 respectively to balance interconnect capacitances between different channels. With equalized total load capacitance across all the four channels, the sensor outputs feature uniform channel response and minimized crosstalk. Note that, in one embodiment, 704-4 may be omitted since the associated interconnect 703-4 has the largest capacitance. Note also that, although the areas of the traces 703-1, 703-2 etc. are usually the biggest factors determining the bandwidths of the outputs, other factors including the doping of the silicon beneath traces 703-1, 703-2 etc., the resistance of any polysilicon interconnects, and the transconductances of transistors such as M3 shown in FIG. 5 may result in different outputs having different bandwidths in absence of metal pieces 704-1, 704-2 etc. The areas of metal pieces 704-1, 704-2 etc. may be chosen so as to compensate for these and other factors. In an alternative embodiment, the second stage transistors may be placed close to the first stage transistors with different length traces connecting those transistors to the metal pads such as OS1, OS2, OS3 and OS4.

FIG. 8A illustrates exemplary voltage waveforms and timing configurations of clock signals to drive the on-chip dual-column-parallel readout structure in accordance with one embodiment of the present invention. Voltage and time are plotted in arbitrary units. Voltages of different clock signals are not necessarily plotted to the same scale.

Although a three-phase CCD array sensor is utilized in the particular embodiment illustrated in FIG. 8A, the present clock driving scheme can also apply to other CCD area sensors and line sensors. Each pixel of the three-phase CCD sensor comprises three polysilicon gates driven by continuous phase clocks P1V, P2V, and P3V, respectively. The phase clocks are synchronized to a line clock (not shown), which controls charge transfer from a row of pixels to the readout structure. Each of the three clock signals is shifted in phase by 120 degrees relative to the other two clock signals, enabling charge transfer down the column as briefly described in FIG. 4. U.S. Pat. No. 7,609,309, entitled "Continuous clocking of TDI sensors", issued on Oct. 27, 2009 and U.S. Pat. No. 7,952,633, entitled "Apparatus for continuous clocking of TDI sensors", issued on May 31, 2011 describe additional aspects and details of the continuous clock driving scheme. Both patents are incorporated herein by reference.

Referring to the dual-column-parallel readout structure depicted in FIG. 5 and its clock driving scheme illustrated in FIG. 8A, clock signal VB drives the row of buffer gates 503, clock signals C1 and C2 drive the two rows of paired transfer gates 504, clock signal SG drives the row of common summing gates 505, and clock signal RG drives the gates of reset transistors such as 508. These clocks are synchronized to a free-running internal clock ADC-C of an ADC in an off-chip signal processing circuit. During a clock cycle, clock signal VB increases gradually from low to high and drops sharply after it reaches a peak value. In a conventional CCD, image charges transfer from pixels to a horizontal output register (or to buffer gates similar to 503) at a constant rate because clock signals similar to P1V, P2V, P3V, and VB run at a constant frequency. In one embodiment that includes two rows of buffer gates, a second buffer gate clock signal (not shown), approximately 180° out of phase with VB, drives that second row. In another embodiment with more than two rows of buffer gates, odd-numbered rows (starting with the row of buffer gates adjacent to the last row of pixels) are driven by clock signal VB, and even-numbered rows are driven by a clock signal approximately 180° out of phase with VB. An advantage of using an even number of rows of buffer gates is that the two buffer gate clock signals, being approximately 180° out of phase with one another, is that the currents from these clock signals approximately cancel minimizing noise currents flowing in the sensor. In one embodiment of the present invention complimentary clock signals C1 and C2 sequentially move image charge from odd and even columns into common summing gate 505, while clock signal SG transmits the image charge to the floating diffusion at twice the frequency of phase clocks P1V, P2V, and P3V. Clock signal RG resets the voltage at the floating diffusion in preparation for the image charge at the next clock cycle. Clock signal ST is generated by a timing generator and is synchronized to ADC-C. After clock signal RG resets the voltage at the floating diffusion, clock signal ST triggers correlated double sampling (CDS) during which the sensor output is sampled and prepared for digitization.

In an inspection system, the image acquisition needs to be synchronized with the motion of the sample. In such a system the image sensor operates with clock jitter or a varying phase mismatch between a line clock and the ADC clock ADC-C. This can cause image blur and image lag, which are undesirable and may degrade the sensitivity of the inspection. In one preferred embodiment illustrated in FIG. 8A, clock signals VB, C1, and C2 continuously change their frequency to track the image, while the on-chip amplifier and off-chip signal processing circuits operate at a constant frequency. Consider a nominal 10 MHz line clock frequency for illustrative purposes. The frequency of phase clocks P1V, P2V, and P3V is set to 10 MHz. In this example, the frequency of clock signals SG and RG is set to 22 MHz, which is 10% higher than twice the line clock frequency. In order to stay synchronized with the line clock frequency, clock signal VB skips a half clock cycle for every five line clock cycles as shown near time 801. Complimentary clock signals C1 and C2 also skip half clock cycles accordingly. Since reset clock RG runs 10% higher than twice the line clock frequency, there is one redundant RG clock cycle for every five line clock cycles. Other ratios of reset clock frequency to line clock frequency are possible, as long as the reset clock frequency is greater than twice the highest line clock frequency. This scheme can accommodate, by appropriate choice of reset clock frequency, a line clock frequency that varies slightly because, for example, it is synchronized to the motion of a sample moving at a slightly varying speed. The clock jitter is compensated for by redundant RG clock cycles in which image charge does not transfer to the floating diffusion. As a result, this line clock synchronization method can keep the clock phase mismatch within desired limits and mitigate image blur and image lag. The data corresponding to the redundant RG clock cycles need not be digitized, or may be digitized and discarded, whichever is more convenient.

FIG. 8B illustrates exemplary voltage waveforms and timing configurations of clock signals to drive the on-chip dual-column-parallel readout structure and off-chip signal processing circuits in accordance with another embodiment of the present invention. The voltage and time are plotted in arbitrary units. The voltages of clock signals are not necessarily plotted to the same scale. Although a three-phase CCD array sensor is utilized in the particular embodiment illustrated in FIG. 8B, the present clock driving scheme can also apply to other CCD area sensors and line sensors. The individual clock signals are labeled similarly to FIG. 8A and perform substantially similar functions, but their relative timing is different as explained below.

For illustrative purposes, a free-running nominal 10 MHz line clock and a 200 MHz ADC clock ADC-C are shown in FIG. 8B. The effect of a line clock with an exaggerated frequency sweep of 50% is shown to clearly illustrate the invention. In a typical inspection system, line clock frequency variations might be a few percent or smaller. Clock signals P1V, P2V, and P3V are synchronized to the line clock, whereas clock signals VB, C1, C2, SG, and RG are synchronized to the ADC clock ADC-C. The clock signals operate as depicted in FIG. 8B. Clock signal ST sweeps from 20 MHz to 10 MHz to match the changing line clock that sweeps from 10 MHz to 5 MHz. Accordingly, clock signals VB, C1, and C2 sweep from 10 MHz to 5 MHz, and clock signals SG and RG sweep from 20 MHz to 10 MHz. As the line clock frequency reduces, the off-chip signal processing circuit corrects the phase mismatch between the line clock and the ADC clock and synchronously reads the sensor output. The ADC clock ADC-C operates at a constant frequency of 200 MHz in this illustrative embodiment. In this embodiment, redundant RG clock cycles are not needed.

The embodiments illustrated in FIGS. 8A and 8B utilize a constant frequency for the ADC clock ADC-C, a constant pulse width for reset gate RG, and a constant delay between reset gate RG and the rising edge of ST that triggers data sampling. This combination results in feedthroughs of the reset pulses to the output signals and settling times of the output signals that do not change significantly even though the line clock rate is varying. Since the feedthroughs are constant, the feedthrough can be measured, for example from dark pixels or dark images, and subtracted from image signals, resulting in more accurate images.

FIG. 8C illustrates exemplary voltage waveforms and timing configurations of clock signals to drive the on-chip dual-column-parallel readout structure and off-chip signal processing circuits in accordance with yet another embodiment of the present invention. The voltage and time are plotted in arbitrary units. The voltages of clock signals are not necessarily plotted to the same scale. Although a three-phase CCD array sensor is utilized in the particular embodiment illustrated in FIG. 8C, the present clock driving scheme can also apply to other CCD area sensors and line sensors. The individual clock signals are labeled similarly to FIGS. 8A and 8B and perform substantially similar functions, but their relative timing is different as explained below.

For illustrative purposes, clock signals for a system with a free-running nominal 10 MHz line clock and a 200 MHz ADC clock are shown. The line clock is shown with an exaggerated frequency sweep of 50% to clearly illustrate the invention. In a typical inspection system, line clock frequency variations might be a few percent or smaller. Clock signals P1V, P2V, and P3V are synchronized to the line clock, whereas clock signals VB, C1, C2, SG, and RG are synchronized to the ADC clock ADC-C. The clock signals operate as depicted in FIG. 8C. The ADC clock ADC-C sweeps from 200 MHz to 100 MHz to track the changing line clock frequency. Accordingly, clock signals VB, C1, and C2 sweep from 10 MHz to 5 MHz, and clock signals SG and RG sweep from 20 MHz to 10 MHz. Similar to the embodiment described in FIG. 8B, the pixel data rate tracks the line clock frequency so that the readout of sensor output remains synchronized to the line clock. In contrast to embodiment shown in FIG. 8B in which the CCD clock frequencies sweep, but the ADC clock ADC-C is kept constant, FIG. 8C depicts an embodiment in which the clock frequencies of CCD and ADC clocks all sweep.

In the illustrative examples depicted in FIGS. 8A, 8B and 8C, clocks C1 and C2 that drive the transfer gates are shown as rectangular pulses. In preferred embodiments, these clocks are shaped so as to reduce noise while ensuring efficient high-speed signal transfer. Rise and fall times of other clock signals are also controlled so as to ensure efficient charge transfer and to minimize noise. In one embodiment, clocks C1 and C2 have approximately half sine-wave shapes similar to those illustrated for buffer clock VB, but at twice the frequency. Since clocks C1 and C2 are substantially 180° out of phase with each other, the currents that result from these clocks approximately cancel one another, reducing noise that might degrade the signal-to-noise ratio of the image.

FIGS. 8A, 8B and 8C illustrate clock waveforms and timing for reading out each individual pixel of the image sensor as a separate signal. As long as the full-well capacity of the summing and output gates is large enough compared with the signal level, it is also possible to sum pairs of adjacent pixels by transferring the signal under each summing gate to the corresponding output gate and floating diffusion once per line clock rather than twice per line clock. Image rows may be summed together by, for example, transferring two lines into the buffer gates before transferring the signal under buffer gates to the first row of transfer gates. Systems and methods described in U.S. patent application Ser. No. 15/210,056 entitled "Dark-Field Inspection Using a Low-Noise Sensor", filed on Jul. 14, 2016 by Chuang et al., may be used in combination with the sensor described herein. This patent application is incorporated herein by reference.

Figure 9:
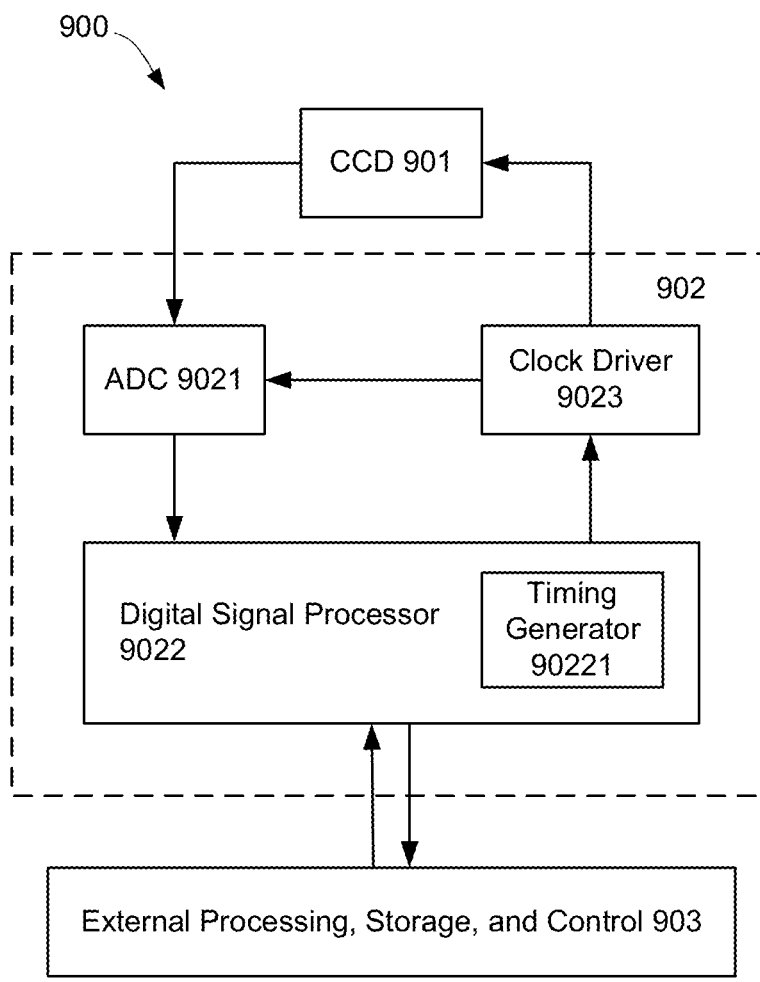
FIG. 9 illustrates an exemplary apparatus for driving a dual-column-parallel CCD image sensor and off-chip signal processing circuits with synchronization of the image sensor readout.

FIG. 9 is a simplified diagram of an apparatus 900 that can implement features and methodologies described herein. The apparatus includes a CCD image sensor 901 which comprises one of the dual-column-parallel CCD sensors disclosed herein, off-chip signal processing circuits 902, and external storage, processing, and control circuits 903. CCD sensor 901 detects incident radiation, converts photo-generated electrons to voltage, and outputs the voltage signal to off-chip signal processing circuits 902. For brevity only function blocks necessary to explain the present invention are depicted in the off-chip signal processing circuits 902. These include ADC 9021, digital signal processor 9022, and clock driver 9023. ADC 9021 comprises CDS and ADC circuits and digitizes the CCD analog output signals. A digital output of ADC 9021 is sent to digital signal processor 9022 for post-processing and, optionally, data compression. A timing generator 90221 incorporated in digital signal processor 9022 generates clock signals, which are buffered by clock driver 9023 to control CCD sensor 901 and ADC 9021. For example, clock driver 9023 may provide clock signals P1V, P2V, P3V, VB, C1, C2, SG, RG, ST, and ADC-C as described above and illustrated in FIGS. 8A, 8B, and 8C. Digital signal processor 9022 interfaces with external storage, processing, and control circuits 903 for further signal processing, control and data transfer, such as clock synchronization.

Note that the apparatus depicted in FIG. 9 may incorporate the waveform generator described in U.S. Pat. No. 9,347,890, entitled "A Low-Noise Sensor and an Inspection System Using a Low-Noise Sensor", to Brown et al., and/or the apparatus may implement a method described in that application. The '890 patent is incorporated herein by reference.

Buffer gates, transfer gates, summing gates, output gates, readout gates, floating diffusion and output amplifiers are well known in CCD image sensors and will not be described in more detail here. The configurations shown in FIGS. 4, 5, 6, and 7 are merely by way of example to explain the operation of the dual-column-parallel CCD sensor. Different configurations of the readout structure are possible without departing from the scope of the invention. In one exemplary embodiment one or more transfer gate pairs with one or more buffer gates could be used. In another exemplary embodiment, three transfer gates may be connected to one summing gate. In this exemplary embodiment, each column would comprise three transfer gates, and three-phase clocks could be used to sequentially clock the signal from each column into the summing gate. These three-phase clocks would be substantially 120° out of phase with respect to one another. Such a sensor might be described as a three-column parallel CCD sensor, but it would operate in a substantially similar manner to the dual-column parallel CCD sensor described herein and is within the scope of the present invention.

In another exemplary embodiment a self-aligned floating diffusion with a polysilicon contact connected to on-chip amplifier could be used. In yet another exemplary embodiment, metal interconnects of on-chip amplifier may be optimized to equalize channel response and minimize crosstalk. Details of commonly used semiconductor manufacturing processes that are not directly relevant to the invention are not included in order to avoid complicating the description.

The various embodiments of the structures and methods of this invention that are described above are illustrative only of the principles of this invention and are not intended to limit the scope of the invention to the particular embodiments described. For example, one or more CCD array sensors, including three-phase sensors or other multi-phase sensors, and/or CCD line sensors may be utilized in an inspection system to inspect a sample.

The image sensors described herein may be incorporated into a module or system such as one described in U.S. Pat. No. 8,754,972, entitled "Integrated multi-channel analog front end and digitizer for high speed imaging applications", issued on Jun. 17, 2014 to Brown et al. This patent is incorporated herein by reference.

It is also to be understood that where sensors or methods are described as detecting light that these descriptions may also apply to detecting electromagnetic radiation of different wavelengths including infra-red, visible light, ultra-violet, extreme UV and X-rays, and to detecting charged particles such as electrons.

Thus, the invention is limited only by the following claims and their equivalents.

The invention claimed is:

1. A method of inspecting a sample, the method comprising:
   directing and focusing radiation onto the sample;
   receiving radiation from the sample and directing received radiation to an image sensor, the sensor comprising a dual-column-parallel CCD including an array of pixels arranged in a plurality of rows and a plurality of associated pairs of adjacent columns, each said associated pair including a first column and a second column;
   moving the sample relative to the radiation simultaneously with said receiving;
   driving the image sensor with line clock signals that are synchronized to the motion of the sample relative to the radiation, the line clock signals causing first and second charges to be transferred from one said row of the image sensor to an adjacent said row along the first and second columns, respectively, of each associated pair of columns;

driving a row of buffer gates of the image sensor with a buffer clock signal, the buffer clock signal causing said first and second charges to be transferred from an edge row of the first and second columns of each associated pair of columns to first and second buffer gates of the row of buffer gates;

driving with a first transfer clock signal both a first transfer gate in a first row of transfer gates disposed over the first column of each associated pair of columns, and a first fourth transfer gate in a second row of transfer gates disposed over the second column of each associated pair of columns;

driving with a second transfer clock signal both a second transfer gate in the first row of transfer gates disposed over the second column of each associated pair of columns, and a third transfer gate in the second row of transfer gates disposed over the first column of each associated pair of columns;

utilizing a readout circuit including multiple output structures, each said output structure including an analog-to-digital converter (ADC) coupled to a corresponding said associated pair of columns and configured to convert said first and second charges transferred along the first and second columns of said corresponding associated pair of columns to first and second digital numbers, respectively; and driving the ADC with a clock frequency greater than twice a frequency of the line clock signals;

wherein the first transfer clock signal causes said first charge to be transferred from the first transfer gate to the third transfer gate during a first time period, and wherein the second transfer clock signal causes said second charge to be transferred from the second transfer gate to the fourth transfer gate during a second time period.

2. The method of claim 1 wherein the first transfer clock signal further causes a third charge to be transferred from the fourth transfer gate in the second row of transfer gates to a summing gate of said corresponding output structure during said first time period, and wherein the second transfer clock signal further causes said first charge to be transferred from the third transfer gate in the second row of transfer gates to the summing gate of said corresponding output structure during said second time period.

3. The method of claim 1, further comprising driving a reset gate of each said corresponding output structure with a constant pulse width, the reset gate being connected to a floating diffusion of said each corresponding output structure, which is configured to receive charges from one of the summing gate of said each corresponding output structure and an output gate connected to the summing gate of said each corresponding output structure, wherein driving said reset gate includes utilizing a reset-gate pulse to cause the reset gate to reset said floating diffusion to a reset voltage; and triggering the ADC to generate a corresponding said digital number at a constant time interval after the reset-gate pulse.

4. The method of claim 1 further comprising driving a fifth transfer gate in a third row of transfer gates of the image sensor with the first transfer clock signal, driving a sixth transfer gate in the third row of transfer gates with the second transfer clock signal, and driving seventh gates in the first, second and third rows of transfer gates with a third transfer clock signal.

5. The method of claim 1, wherein a frequency of the line clocks varies as the speed of the motion of the sample relative to the radiation varies.

6. The method of claim 5, further comprising pausing or skipping one cycle of a buffer clock signal to keep the buffer clock signal synchronized with the line clock.

7. The method of claim 5, further comprising slowing or stretching one cycle of a buffer clock signal to keep the buffer clock signal synchronized with the line clock.

8. An inspection system for inspecting a sample, the inspection system comprising:

a radiation source generating radiation;

optics for directing and focusing radiation onto the sample, receiving radiation reflected or scattered from the sample and directing the received radiation to an image sensor, the image sensor comprising a dual-column-parallel CCD;

a computing system for controlling the inspection system, receiving image data from the image sensor, and analyzing said image data to locate a defect on, or measure a dimension of, the sample;

wherein the dual-column-parallel CCD comprises a rectangular or square array of pixels arranged in a plurality of associated pairs of adjacent pixel columns, each said associated pair including a first pixel column and a second pixel column; and a readout circuit including multiple output structures, each said output structure configured to receive charges from a corresponding said associated pair of adjacent pixel columns, each said output structure comprising:

a first row of transfer gates coupled to receive first charges from a first pixel of said first pixel column and second charges from a second pixel of said second pixel column, and a second row of transfer gates, the second row of transfer gates configured to receive said first and second charges from the first row of transfer gates;

a summing gate configured to alternately receive said first and second charges from the second row of transfer gates; and an output circuit configured to alternately receive said first and second charges charge from said summing gate and to alternately transmit said first and second charges to a single floating diffusion and a single output amplifier, whereby said single floating diffusion and said single output amplifier are shared by said first and second pixel columns of said associated pair of adjacent pixel columns, wherein the first and second rows of transfer gates and said associated pair of adjacent pixel columns are effectively cross-coupled such that a first transfer gate control signal applied to a first transfer gate disposed in the first row and the first pixel column is substantially simultaneously applied to a fourth transfer gate disposed in second row and the second pixel column, and such that a second transfer gate control signal applied to a second transfer gate disposed in the first row and the second pixel column is substantially simultaneously applied to a third transfer gate disposed in the second row and the first pixel column.

9. The inspection system of claim 8, wherein the optics are further configured to illuminate a line on the sample.

10. The inspection system of claim 8, wherein the optics are further configured for both normal and oblique illumination of the sample.

11. The inspection system of claim 10, wherein the sample comprises an unpatterned wafer.

12. The inspection system of claim 10, wherein each said output structure further comprises a row of buffer gates configured to receive said first and second charges from said first and second pixels of said first and second pixel columns, and to transmit said first and second charges to the first row of transfer gates.

* * * * *